(12) United States Patent
Smith et al.

(10) Patent No.: US 9,067,964 B2
(45) Date of Patent: Jun. 30, 2015

(54) COMPLEX AND METHOD FOR ENHANCING NUCLEAR DELIVERY

(75) Inventors: Edvard Smith, Stockholm (SE); Pedro Moreno, Huddinge (SE); Roger Strömberg, Huddinge (SE); Malgorzata Wenska, Uppsala (SE)

(73) Assignee: Oligomer Sciences AB, Djursholm (SE)

( * ) Notice: Subject to any disclaimer, the term of this patent is extended or adjusted under 35 U.S.C. 154(b) by 306 days.

(21) Appl. No.: 13/140,070

(22) PCT Filed: Dec. 17, 2009

(86) PCT No.: PCT/SE2009/051450
§ 371 (c)(1),
(2), (4) Date: Sep. 2, 2011

(87) PCT Pub. No.: WO2010/071587
PCT Pub. Date: Jun. 24, 2010

(65) Prior Publication Data
US 2011/0306138 A1 Dec. 15, 2011

Related U.S. Application Data

(60) Provisional application No. 61/138,925, filed on Dec. 18, 2008.

(51) Int. Cl.
| | |
|---|---|
| *A01N 43/04* | (2006.01) |
| *A61K 31/70* | (2006.01) |
| *C07H 19/167* | (2006.01) |
| *A61K 31/7056* | (2006.01) |
| *A61K 31/7084* | (2006.01) |
| *A61K 31/7076* | (2006.01) |
| *A61K 31/7064* | (2006.01) |
| *A61K 31/708* | (2006.01) |
| *A61K 31/7042* | (2006.01) |
| *A61K 31/706* | (2006.01) |
| *A61K 31/7052* | (2006.01) |
| *A61K 31/7115* | (2006.01) |
| *A61K 31/712* | (2006.01) |
| *C07H 19/20* | (2006.01) |
| *C07H 19/207* | (2006.01) |
| *C07H 21/02* | (2006.01) |

(52) U.S. Cl.
CPC .......... *C07H 19/167* (2013.01); *A61K 31/7056* (2013.01); *A61K 31/7084* (2013.01); *A61K 31/7076* (2013.01); *A61K 31/7064* (2013.01); *A61K 31/708* (2013.01); *A61K 31/7042* (2013.01); *A61K 31/706* (2013.01); *A61K 31/7052* (2013.01); *A61K 31/7115* (2013.01); *A61K 31/712* (2013.01); *C07H 19/20* (2013.01); *C07H 19/207* (2013.01); *C07H 21/02* (2013.01)

(58) Field of Classification Search
None
See application file for complete search history.

(56) References Cited

U.S. PATENT DOCUMENTS

2010/0261231 A1* 10/2010 Kore et al. .................. 435/91.3

FOREIGN PATENT DOCUMENTS

| WO | 98/34942 | 8/1998 |
|---|---|---|
| WO | 2008/016473 | 2/2008 |

OTHER PUBLICATIONS

Sekine, M. et al. (Tetrahedron Letters, 2003, 44 (8), 1703-1707.*
Bhindi, R. et al. (American Journal of Pathology 171 (4), 2007,1079-1088.*
Sekine, M. et al. Tetrahedron Letters, 2003, 44 (8), 1703-1707.*
Bhindi, R. et al. American Journal of Pathology 171 (4), 2007, 1079-1088.*
Patani, G.A. et al. (Chemical Reviews, 1996, 96 (8), pp. 3147-3176.*
Goodchild J. Bio conjugate Chemistry, 1990, 1,(3), 165-87.*
Kadokura, M. et al. Tetrahedron Letters, 2001, 42 (50), pp. 8853-8856.*
Rollehagen et al Can J Physiol and Pharmacology, 2006, 86, 367-376.*
Plessel et al Molecular and Cellular Biology, 1994, 4160-4172.*
Gorlich, D. and Mattaj, I.W. (1996) Nucleocytoplasmic transport. Science, 271,1513-1518.
Lange, A., Mills, R.E., Lange, C.J., Stewart, M., Devine, S.E and Corbett, A.H. (2006) Classical nuclear localization signals: definition, function, and interaction with importin alpha. J Biol Chem, 282, 5101-5105.
Jakel, S. and Gorlich, D. (1998) Importin beta, transportin, RanBP5 and RanBP7 mediate nuclear import of ribosomal proteins in mammalian cells. EMBO J., 17, 4491-4502.
Gorlich, D., Pante, N., Kutay, U., Aebi, U. and Bischoff, F.R (1996) Identification of different roles for RanGDP and RanGTP in nuclear protein import. EMBO J, 15, 5584-5594.
Izaurralde, E., Kutay, U., von Kobbe, C., Mattaj, I.W. and Gorlich, D. (1997) The asymmetric distribution of the constituents of the Ran system is essential for transport into and out of the nucleus. EMBO J, 16, 6535-6547.
Kitao, S., Segref, A., Kast, J., Wilm, M., Mattaj, I.W. and Ohno, M. (2008) A compartmentalized phosphorylation/dephosphorylation system that regulates U snRNA export from the nucleus. Mol Cell Biol, 28, 487-497.

(Continued)

*Primary Examiner* — Patrick Lewis
(74) *Attorney, Agent, or Firm* — Renner, Otto, Boisselle & Sklar, LLP

(57) ABSTRACT

The use of at least one nucleic acid based nuclear localization signal including a natural or synthetic $m_3G$-CAP is shown to increase transmembrane transport of a molecular cargo, in particular large molecules, into the nucleus. The use of natural and synthetic $m_3G$-CAP is disclosed and the effect shown with a natural RNA 5' end nuclear localization signal composed of a 2,2,7-trimethylguanosine CAP ($m_3G$-CAP) coupled to fluorescent Streptavidin in one example, and an antisense oligonucleotide in another. A methylenephosphonate modified $m_3G$-CAP is shown to have improved stability in human serum and in cytosolic extract.

9 Claims, 11 Drawing Sheets

(56) References Cited

OTHER PUBLICATIONS

Golembe, T.J., Yong, J. and Dreyfuss, G. (2005) Specific sequence features, recognized by the SMN complex, identify snRNAs and determine their fate as snRNPs. Mol Cell Biol, 25, 10989-11004.

Yong, J., Golembe, T.J., Battle, D.J., Pellizzoni, L. and Dreyfuss, G. (2004) snRNAs contain specific SMN-binding domains that are essential for snRNP assembly. Mol Cell Biol, 24, 2747-2756.

Friesen, W.J. and Dreyfuss, G. (2000) Specific sequences of the Sm and Sm-like (Lsm) proteins mediate their interaction with the spinal muscular atrophy disease gene product (SMN). J Biol Chem, 275, 26370-26375.

Fischer, U., Liu, Q. and Dreyfuss, G. (1997) The SMN-SIP1 complex has an essential role in spliceosomal snRNP biogenesis. Cell, 90, 1023-1029.

Mouaikel, J., Narayanan, U., Verheggen, C., Matera, A.G., Bertrand, E., Tazi, J. and Bordonne, R. (2003) Interaction between the small-nuclear-RNA cap hypermethylase and the spinal muscular atrophy protein, survival of motor neuron. EMBO Rep, 4, 616-622

Plessel, G., Fischer, U. and Luhrmann, R. (1994) m3g-cap hypermethylation of U1 small nuclear ribonucleoprotein (snRNP) in vitro: evidence that the U1 small nuclear RNA-(guanosine-N2)-methyltransferase is a non-snRNP cytoplasmic protein that requires a binding site on the Sm core domain. Mol Cell Biol, 14, 4160-4172.

Narayanan, U., Ospina, J.K., Frey, M.R., Hebert, M.D. and Matera, A.G. (2002) SMN, the spinal muscular atrophy protein, forms a pre-import snRNP complex with snurportin1 and importin beta. Hum. Mol. Genet., 11, 1785-1795.

Huber, J., Cronshagen, U., Kadokura, M., Marshallsay, C., Wada, T., Sekine, M. and Luhrmann, R. (1998) Snurportin1, an m3G-cap-specific nuclear import receptor with a novel domain structure. EMBO J., 17, 4114-4126.

Mitrousis, G., Olia, A.S., Walker-Kopp, N. and Cingolani, G. (2008) Molecular basis for the recognition of snurportin 1 by importin beta. J Biol Chem, 283, 7877-7884.

Wohlwend, D., Strasser, A., Dickmanns, A. and Ficner, R. (2007) Structural basis for RanGTP independent entry of spliceosomal U snRNPs into the nucleus. J Mol Biol, 374, 1129-1138.

Girard, C., Mouaikel, J., Neel, H., Bertrand, E. and Bordonne, R. (2004) Nuclear localization properties of a conserved protuberance in the Sm core complex. Exp. Cell Res., 299, 199-208.

Fischer, U. and Luhrmann, R. (1990) An essential signaling role for the m3g-cap in the transport of U1 snRNP to the nucleus. Science, 249, 786-790.

Strasser, A., Dickmanns, A., Schmidt, U., Penka, E., Urlaub, H., Sekine, M., Luhrmann, R. and Ficner, R. (2004) Purification, crystallization and preliminary crystallographic data of the m3g-cap-binding domain of human snRNP import factor snurportin 1. Acta Crystallogr. D Biol. Crystallogr., 60, 1628-1631.

Strasser, A., Dickmanns, A., Luhrmann, R. and Ficner, R. (2005) Structural basis for m3G-cap-mediated nuclear import of spliceosomal UsnRNPs by snurportin1. EMBO J., 24, 2235-2243.

Huber, J., Dickmanns, A. and Luhrmann, R. (2002) The importin-beta binding domain of snurportin1 is responsible for the Ran- and energy-independent nuclear import of spliceosomal U snRNPs in vitro. J. Cell Biol., 156, 467-479.

Chen, P., Wang, J., Hope, K., Jin, L., Dick, J., Cameron, R, Brandwein, J., Minden, M. and Reilly, R.M. (2006) Nuclear localizing sequences promote nuclear translocation and enhance the radiotoxicity of the anti-CD33 monoclonal antibody HuM195 labeled with 111In in human myeloid leukemia cells. J Nucl Med, 47, 827-836.

Dean, D.A, Dean, B.S., Muller, S. and Smith, L.C. (1999) Sequence requirements for plasmid nuclear import. Exp Cell Res, 253, 713-722.

Wagstaff, K.M. and Jans, D.A (2007) Nucleocytoplasmic transport of DNA: enhancing non-viral gene transfer. Biochem J, 406, 185-202.

Collas, P., Husebye, H. and Alestrom, P. (1996) The nuclear localization sequence of the SV40 T antigen promotes transgene uptake and expression in zebrafish embryo nuclei. Transgenic Res, 5, 451-458.

Zanta, M.A., Belguise-Valladier, P. and Behr, J.P. (1999) Gene delivery: a single nuclear localization signal peptide is sufficient to carry DNA to the cell nucleus. Proc Natl Acad Sci USA, 96, 91-96.

Branden, L.J., Mohamed, A.J. and Smith, C.I.E. (1999) A peptide nucleic acid-nuclear localization signal fusion that mediates nuclear transport of DNA Nat Biotechnol, 17, 784-787.

Branden, L.J., Christensson, B. and Smith, C.I.E. (2001) in vivo nuclear delivery of oligonucleotides via hybridizing bifunctional peptides. Gene Ther, 8, 84-87.

Neves, C., Byk, G., Scherman, D. and Wils, P. (1999) Coupling of a targeting peptide to plasmid DNA by covalent triple helix formation. FEBS Lett, 453, 41-45.

Ludtke, J.J., Zhang, G., Sebestyen, M.G. and Wolff, J.A (1999) A nuclear localization signal can enhance both the nuclear transport and expression of 1 kb DNA. J. Cell. Sci., 112 ( Pt 12), 2033-2041.

Subramanian, A., Ranganathan, P. and Diamond, S.L. (1999) Nuclear targeting peptide scaffolds for lipofection of nondividing mammalian cells. Nat Biotechnol, 17, 873-877.

Sawai, H., Wakai, H. and Nakamura-Ozaki, A. (1999) Synthesis and Reactions of Nucleoside 5'-Diphosphate Imidazolide. A Nonenzymatic Capping Agent for 5'-Monophosphorylated Oligoribonucleotides in Aqueous Solution. J Org Chem, 64, 5836-5840.

Sekine, M., Kadokura, M., Satoh, T., Seio, K., Wada, T., Fischer, U., Sumpter, V. and Luhrmann, R. (1996) Chemical Synthesis of a 5'-Terminal TMG-Capped Triribonucleotide m(3)(2,2,7)G(5)(')pppAmpUmpA of U1 RNA. J Org Chem, 61, 4412-4422.

Li, P., Xu, Z., Liu, H., Wennefors, C.K., Dobrikov, M.I., Ludwig, J. and Shaw, B.R. (2005) Synthesis of alpha-P-modified nucleoside diphosphates with ethylenediamine. J Am Chem Soc, 127, 16782-16783.

Ludwig, J. and Eckstein, F. (1989) Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J Org Chem, 54, 631-635.

Li, P. and Shaw, B.R (2004) Convenient synthesis of nucleoside borane diphosphate analogues: deoxy- and ribonucleoside 5'-P(alpha)-boranodiphosphates. J Org Chem, 69, 7051-7057.

Han, Q., Gaffney, B.L. and Jones, R.A. (2006) One-flask synthesis of dinucleoside tetra- and pentaphosphates. Org Lett, 8, 2075-2077.

Kang, S.H., Cho, M.J. and Kole, R. (1998) Up-regulation of luciferase gene expression with antisense oligonucleotides: implications and applications in functional assay development. Biochemistry, 37, 6235-6239.

Mattaj, I.W. (1986) Cap trimethylation of U snRNA is cytoplasmic and dependent on U snRNP protein binding. Cell, 46, 905-911.

Pante, N. (2006) Use of intact Xenopus oocytes in nucleocytoplasmic transport studies. Methods Mol Biol, 322, 301-314.

Bonner, W.M. (1975) Protein migration into nuclei. II. Frog oocyte nuclei accumulate a class of microinjected oocyte nuclear proteins and exclude a class of microinjected oocyte cytoplasmic proteins. J Cell Biol, 64, 431-437.

Dabauvalle, M.C. and Franke, W.W. (1982) Karyophilic proteins: polypeptides synthesized in vitro accumulate in the nucleus on microinjection into the cytoplasm of amphibian oocytes. Proc Natl Acad Sci USA, 79, 5302-5306.

Stefanovic, B., Hackl, W., Luhrmann, R. and Schumperli, D. (1995) Assembly, nuclear import and function of U7 snRNPs studied by microinjection of synthetic U7 RNA into Xenopus oocytes. Nucleic Acids Res, 23, 3141-3151.

Rollenhagen, C., Muhlhausser, P., Kutay, U. and Pante, N. (2003) Importin beta-depending nuclear import pathways: role of the adapter proteins in the docking and releasing steps. Mol Biol Cell, 14, 2104-2115.

Rollenhagen, C. and Pante, N. (2006) Nuclear import of spliceosomal snRNPs. Can J Physiol Pharmacol, 84, 367-376.

Rongbin Ge, Mathias G. Svahn, Oscar E. Simonson, Abdalla J. Mohamed, Karin E. Lundin, C. I. Edvard Smith, Sequence-specific inhibition of RNA polymerase III-dependent transcription using Zorro locked nucleic acid (LNA), The Journal of Gene Medicine, 2007, vol. 10, Issue 1, pp. 101 -109.

(56) References Cited

OTHER PUBLICATIONS

Sekine, M. et al. (2003) Synthesis of TMG-capped RNA-DNA chimeric oligonucleotides, Tetrahedron Letters 44 (8), pp. 1703-1707, p. 1709, left column: first paragraph, last sentence, p. 1703, left column: second paragraph, last sentence, scheme 4: structure 24, abstract.

Bhindi, R. et al. (2007) Brothers in arms: DNA enzymes, short interfering RNA, and the emerging wave of small-molecule nucleic acid-based gene-silencing strategies. American Journal of Pathology 171 (4), pp. 1079-1088, p. 1079, left column: last sentence, p. 1080, left column: line 1—p. 1080, left column: line 24, p. 1085, right column: last paragraph, last sentence, abstract.

Kadokura, M. et al. (2001) Solid-phase synthesis of a 5'-terminal TMG-capped trinucleotide block of U1 snRNA. Tetrahedron Letters 42 (50), pp. 8853-8856, p. 8855, left column: last paragraph, figure 1, scheme 2: compound 1.

Kadokura, M. et al. (2000) Synthesis of 4-thiouridine, 6-thioinosine, and 6-thioguanosine 3',5'-0-bisphosphates as donor molecules for RNA ligation and their application to the synthesis of photoactivatable TMG-capped U1 snRNA fragments. Journal of Organic Chemistry 65 (17), pp. 5104-5113, p. 5104, right column: last paragraph, scheme 4: compound 30, abstract.

Patani, G.A. et al. (1996) Bioisosterism: A rational approach in drug design. Chemical Reviews 96 (8), pp. 3147-3176, table 8 and figure 10; table 20 and figure 24.

Freeman, S. et al. (1996) Acyclic Nucleosides as Antiviral Compounds. Applied Biochemistry and Biotechnology—Part B Molecular Biotechnology 5 (2), pp. 125-137, p. 127: structures 18 and 19, p. 133: conclusions, abstract.

Worch, R. et al. (2005) Specificity of recognition of mRNA 5' cap by human nuclear cap-binding complex. RNA 11 (9), pp. 1355-1363, cheme 1 and table 1, abstract.

Fischer, U. et al. (1991) Diversity in the signals required for nuclear accumulation of U snRNPs and variety in the pathways of nuclear transport. Journal of Cell Biology 113 (4), pp. 705-714, table 1: first compound, abstract.

Moreno, P.M.D. et al. (2009) A synthetic snRNA m3G-CAP enhances nuclear delivery of exogenous proteins and nucleic acids. Nucleic Acids Research 37 (6), pp. 1925-1935, the whole document.

International Search Report for corresponding International Application No. PCT/SE2009/051450 mailed Mar. 17, 2010.

Written Opinion for corresponding International Application No. PCT/SE2009/051450 mailed Mar. 17, 2010.

PCT International Preliminary Report on Patentability for corresponding International Application No. PCT/SE2009/051450 mailed Mar. 17, 2010.

Moreno et al., "A synthetic snRNA m3G-CAP enhances nuclear delivery of exogenous proteins and nucleic acids", Nucleic Acids Research, 2009, vol. 37, No. 6, pp. 1925-1935.

* cited by examiner

COMPLEX AND METHOD FOR ENHANCING NUCLEAR DELIVERY

This application is a national phase of International Application No. PCT/SE2009/051450 filed Dec. 17, 2009 and published in the English language, which claims priority to U.S. 61/138,925 filed Dec. 18, 2008.

TECHNICAL FIELD

The present invention relates to the field of molecular biochemistry and medicine, and in particular to a new non-viral vector for transmembrane delivery of therapeutic molecules.

BACKGROUND

Accessing the nucleus through the nuclear membrane poses one of the major obstacles for any therapeutic molecule that is large enough to be excluded due to nuclear pore size limits. Non-viral vector development for gene therapy is a field where mechanisms for improving nucleic acid delivery to the nucleus have been studied but only limited success has so far been achieved. Besides the large size of some nucleic acids, like plasmid DNA, hampering their access to the nuclear compartment, also for small oligonucleotides, the less time they reside in the cytoplasm the less prone they are to degradation processes. Moreover, it also should be beneficial if higher nuclear concentrations could be achieved in some applications. The use of peptide nuclear localization signals (NLS) together with nucleic acids has been one of the most explored formats in trying to achieve better nuclear transfer of genetic material.

Nucleocytoplasmic transport of endogenous molecules is a regulated process where small molecules are able to diffuse through the nuclear pore complex of the nuclear membrane while molecules >40 kDa require the use of a signal and energy-mediated processes. Import of nuclear proteins requires nuclear localization signals (NLS) in the form of specific amino-acid sequences which mediate the interaction with carrier proteins [1]. The best studied NLS sequence is the SV40 large-T antigen. It mediates the interaction between the cargo protein, bearing the NLS signal, and an import receptor consisting of an adaptor protein, importin alpha, which directly binds the NLS signal, and importin beta which is the mediator of the actual import process through the nuclear pores [2].

An archetypical NLS, which is mediating the interaction with several different types of import receptors, is found on the ribosomal L23a protein. This NLS, which has a higher degree of complexity and harbours very basic regions, is thought to have evolved prior to the evolutionary divergence of import receptors [3].

In addition to the cargo and import receptor interactions there are other factors needed in the process of nuclear import. It is the asymmetric distribution of the factors Ran, RCC1, RanGAP1, RanBP1, creating a steep RanGTP gradient across the nuclear envelope that allows the directional movement of the cargo-importin receptor complex to the nucleus [4, 5].

Besides nuclear proteins some RNAs, in the form of small nuclear ribonuclear protein complexes (snRNP), use signals for nuclear import. These RNAs are comprised of the major spliceosomal U snRNAs, such as U1, U2, U4 and U5 and are the major building units of the spliceosomal complex. U snRNAs are transcribed in the nucleus by RNA polymerase II after which they acquire a 7-methylguanosine ($m^7G$) cap structure at their 5' end. This cap structure acts as a nuclear export signal that is recognized by the cap-binding complex (CBC). The CBC complex is in turn recognized by the export receptor CRM1 with the help of PHAX adapter leading ultimately to the nuclear export of the U snRNA [6].

After release in the cytoplasm the U snRNA is recognized by the survival of motor neuron complex (SMN) that directs the proper assembly with a group of Sm proteins [7-10]. Subsequently the $m^7G$ cap is hypermethylated to a trimethylguanosine ($m_3G$) cap structure (FIG. 1) by the small-nuclear-RNA cap hypermethylase [11, 12]. The matured snRNP is then imported back into the nucleus.

This nuclear transport involves two different pathways and two very distinct import signals, both of which, however, recruiting importin beta [13-16]. The first pathway uses a, still poorly defined, import signal present in the Sm core domain of the snRNP formed by the Sm proteins [17]. The second pathway involves the use of the 5' 2,2,7-trimethylated guanosine ($m_3G$) cap structure [18]. The $m_3G$-CAP signal is recognized by the import adaptor protein snurportin (SPN1) [14, 19, 20], which in turn is recognized by importin beta [14-16, 21].

Nuclear import of therapeutic molecules is of great importance for many applications. For example, specific targeting of exogenous proteins, such as antibodies, to the nucleus for the purpose of radioimmunotherapy, is seen as a way to increase cytotoxicity effects in cancer cells [22]. In particular, one of the areas where nuclear targeting has been getting a lot of attention is the gene delivery/gene therapy field. This is especially true in non-viral or synthetic vector development, since these transport systems need to mimic most of the virus strategies used to overcome several cellular barriers of which the nuclear membrane is the ultimate one.

Some approaches to nuclear delivery of nucleic acids, like plasmid DNA, have relied on the DNA sequence itself [23]. A plethora of other types of strategies for nucleic acid delivery has been based, however, on the direct or indirect attachment of NLS peptides to the nucleic acid molecules as a way to promote binding of the importin alpha/importin beta heterodimer to the nucleic acid construct and its subsequent nuclear translocation [24]. The SV40 large T antigene NLS (especially in its shortest form pkkkrkv) has been one of the most employed NLS peptide. It has been associated to DNA via ionic interactions [25]; via chemical coupling [26]; through the use of peptide nucleic acids (PNA) linked to the NLS and bound to DNA in a sequence specific manner [27, 28]; through the use of a triple helix forming oligonucleotide system [29] and by the use of biotinylated DNA bound NLS conjugated streptavidin [30]. An example of another peptide NLS used is the non-classical NLS defined by the M9 sequence, coming from the heterogeneous nuclear ribonucleoprotein (hnRNP) A1, which has been used together with a DNA binding peptide for increased nuclear delivery after lipofection of non-dividing cells [31].

Current means to transport macromolecules, e.g. nucleotides, for example using classical positively charged peptide-based NLS sequences, are not very efficient and there is a need for novel complexes and methods for transmembrane transport with improved specificity, transport capacity and stability.

WO 00/04144 discloses the $m_3G$-CAP specific nucleus import receptor protein and the production and use thereof. The disclosure of WO 00/04144 focuses on the polypeptide, antibodies against it, and nucleic acids encoding the same.

SUMMARY

The present inventors have explored the possibility to use $m_3G$-CAP for the purpose of enhancing nuclear delivery of nucleic acids. It was surprisingly found that by coupling the $m_3G$ pyrophosphate in its active form of imidazolide 5 to a 2'-O-methyl oligoribonucleotide possessing a 5' terminal end, resembling closely U snRNAs in vivo, the nuclear delivery of the oligonucleotide together with a large cargo protein was significantly increased. This nuclear transport was confirmed by microinjections into *Xenopus* oocytes and by a protein transfection method for cultured cells that delivers proteins to the cytosol.

Based on the experiments performed to date, and preliminary observations from ongoing studies, the inventors make available a method and a complex for transmembrane transport of a molecular cargo into the nucleus using at least one non-peptide, nucleic acid based nuclear localization signal as defined in the claims, incorporated herein by reference.

One embodiment of the invention is a complex for facilitating transmembrane transport of a molecular cargo into the nucleus of a mammalian cell, wherein said complex comprises a molecular cargo coupled to at least one nucleic acid based nuclear localization signal, comprising 2,2,7-trimethylguanosine CAP ($m_3G$-CAP) or an analogue thereof.

According to an embodiment, said nuclear localization signal is a synthetic $m_3G$-CAP or an analogue thereof.

According to another embodiment, said molecular cargo is linked by covalent or non-covalent attachment to a modified 2,2,7-trimethyl-guanosineCAP ($m_3G$-CAP) structure as specified in Formula (I)

Acid (LNA), Peptide Nucleic Acid (PNA) or any other backbone modified nucleoside unit.

In another embodiment freely combinable with any of the above, both $R_4$ and $R_5$ are $CH_2$. Alternatively, $R_5$ is O when $R_4$ is $CH_2$, or $R_4$ is O when $R_5$ is $CH_2$.

In yet another embodiment freely combinable with any of the above, the complex further includes phosphorothioate modifications of the compound, as either isomer, at one or more of the positions X, Y and Z.

In yet another embodiment freely combinable with any of the above, said molecular cargo comprises a therapeutic molecule chosen among natural and synthetic peptides, proteins, oligonucleotides, morpholino oligomers or nucleic acids linked to the above structure by a covalent linkage or by non-covalent interaction.

The inventors also make available a method for transmembrane transport of a molecular cargo into the nucleus of a mammalian cell, wherein said molecular cargo is coupled to at least one nucleic acid based nuclear localization signal comprising a 2,2,7-trimethylguanosine CAP ($m_3G$-CAP) structure or an analogue thereof.

According to an embodiment of the method, said nuclear localization signal is a synthetic $m_3G$-CAP or an analogue thereof.

According to an embodiment freely combinable with the above, nuclear delivery of said molecular cargo is achieved by

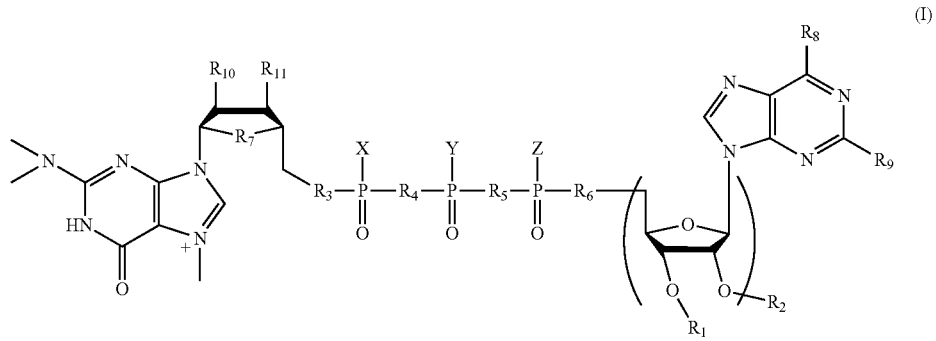

(I)

wherein $R_1$ is a cargo attached directly or a mono-, di or oligonucleotide (modified or unmodified) followed by a cargo unless the cargo is attached through $R_2$ then $R_1$ is a hydroxyl or a phosphate mono or diester;

$R_2$ is methyl or H or any unsubstituted or substituted alkyl group or is a cargo attached directly or a mono-, di or oligonucleotide (modified or unmodified) followed by a cargo;

$R_3$ is O or $CH_2$;
$R_4$ is O or $CH_2$;
$R_5$ is O or $CH_2$;
$R_6$ is O or $CH_2$;
X is OH or SH, or salts thereof;
Y is OH or SH, or salts thereof;
Z is OH or SH, or salts thereof;
$R_7$ is O, or $CH_2$;
$R_8$ is $NH_2$, H, or OH;
$R_9$ is H, $NH_2$ or OH;
$R_{10}$ is OH, or F; and
$R_{11}$ is OH, or $OCH_3$.

In an embodiment freely combinable with the above, the ribose unit in brackets is chosen from a ribose, deoxyribose, a sugar residue or sugar replacement unit of a Locked Nucleic covalent or non-covalent attachment to at least one modified 2,2,7-trimethylguanosineCAP ($m_3G$-CAP) structure as specified in formula I.

According to yet another embodiment freely combinable with any of the above, said molecular cargo comprises a therapeutic molecule chosen among natural and synthetic peptides, proteins, oligonucleotides, morpholino oligomers or nucleic acids linked to the above structure by a covalent linkage or by non-covalent interaction.

The inventors also make available the use of 2,2,7-trimethylguanosine CAP ($m_3G$-CAP) or an analogue thereof for the manufacture of a medicament.

The therapeutic utility of the complex and the method is substantiated in an example where the $m_3G$-CAP was shown to be functionally relevant in achieving an increased splice correction when combining it with an antisense oligonucleotide.

SHORT DESCRIPTION OF THE DRAWINGS

The invention will be disclosed in further detail in the following description, non-limiting examples, and claims, with reference to the attached drawings in which:

Figure 7A:
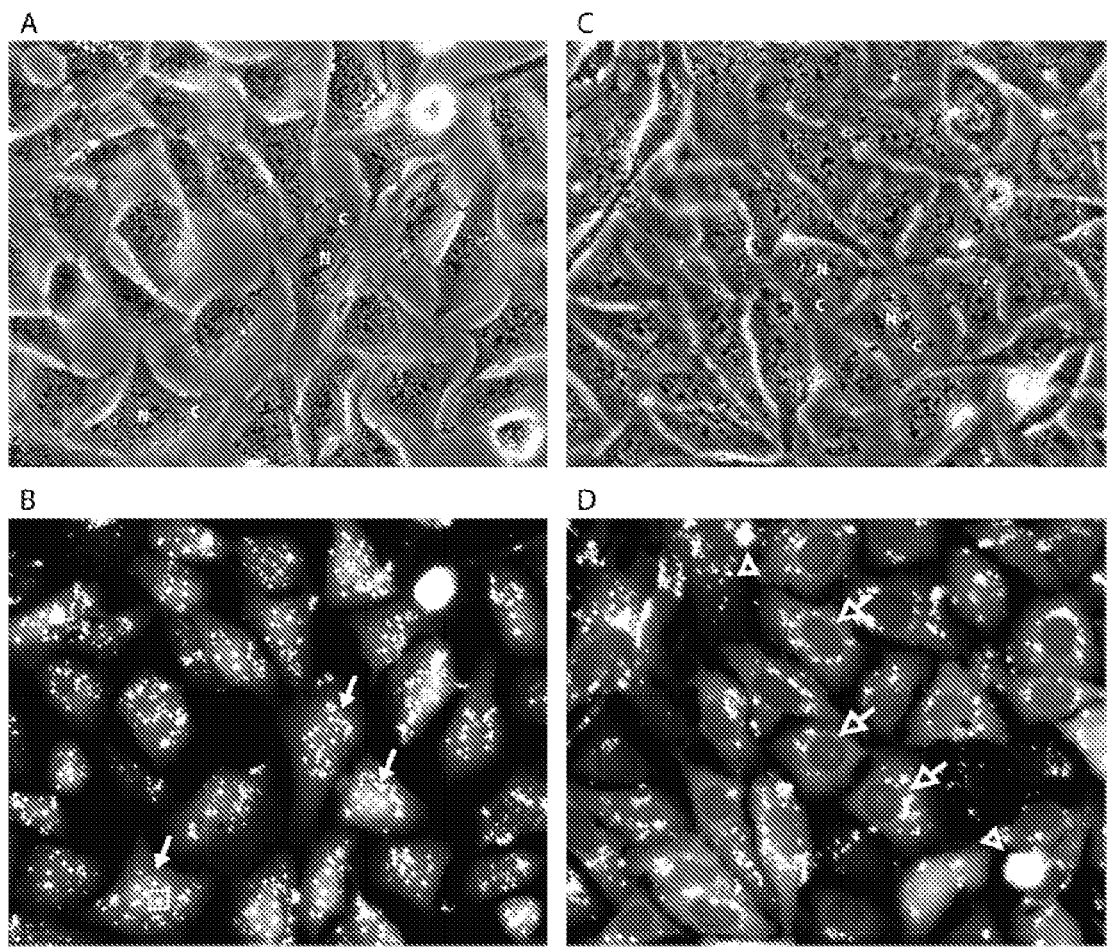

FIG. 7a consists of four phase contrast microscopy pictures, showing the localization of fluorescent Streptavidin when bound to an average of 3-4 biotinylated 2'-O-methyl RNA oligonucleotides with (pictures A, B) or without (pictures C, D) addition of m$_3$G-CAP respectively.

Figure 7B:
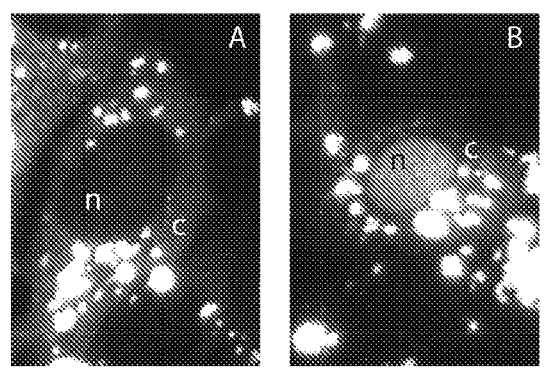

FIG. 7b consist of two fluorescent microscopy pictures; showing lack of nuclear accumulation when LNA oligonucleotides were hybridized to non-capped oligos (picture A), and strong nuclear accumulation when LNA oligonucleotides were hybridized to m$_3$G-capped oligonucleotides (picture B).

Figure 8A:
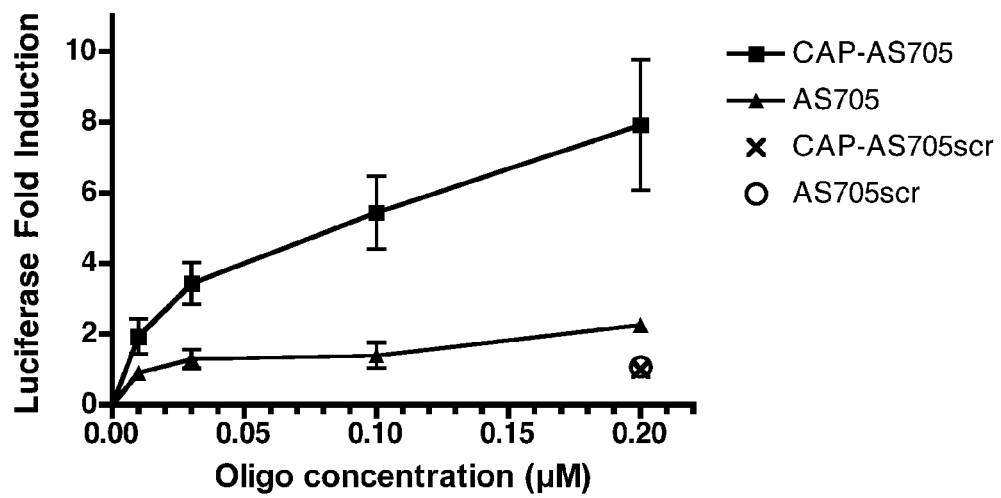

FIG. 8a is a graph showing fold-induction of splice-correction after transfection of HeLa Luc705mut with 2'-O-methyl antisense oligonucleotides at 0.2 μM for 24 h.

Figure 8B:
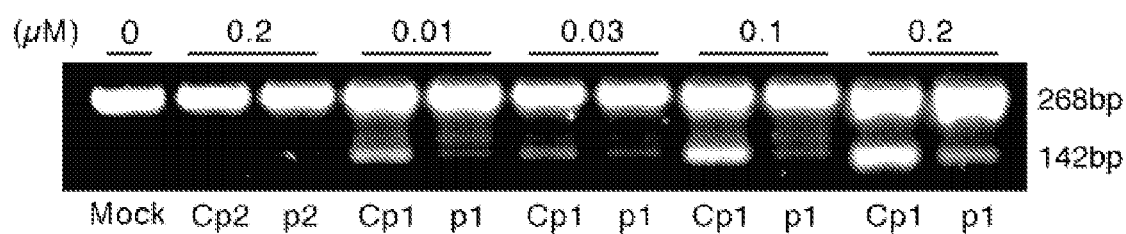

FIG. 8b is a blot showing the result of RT-PCR of the total cellular RNA.

Figure 9:
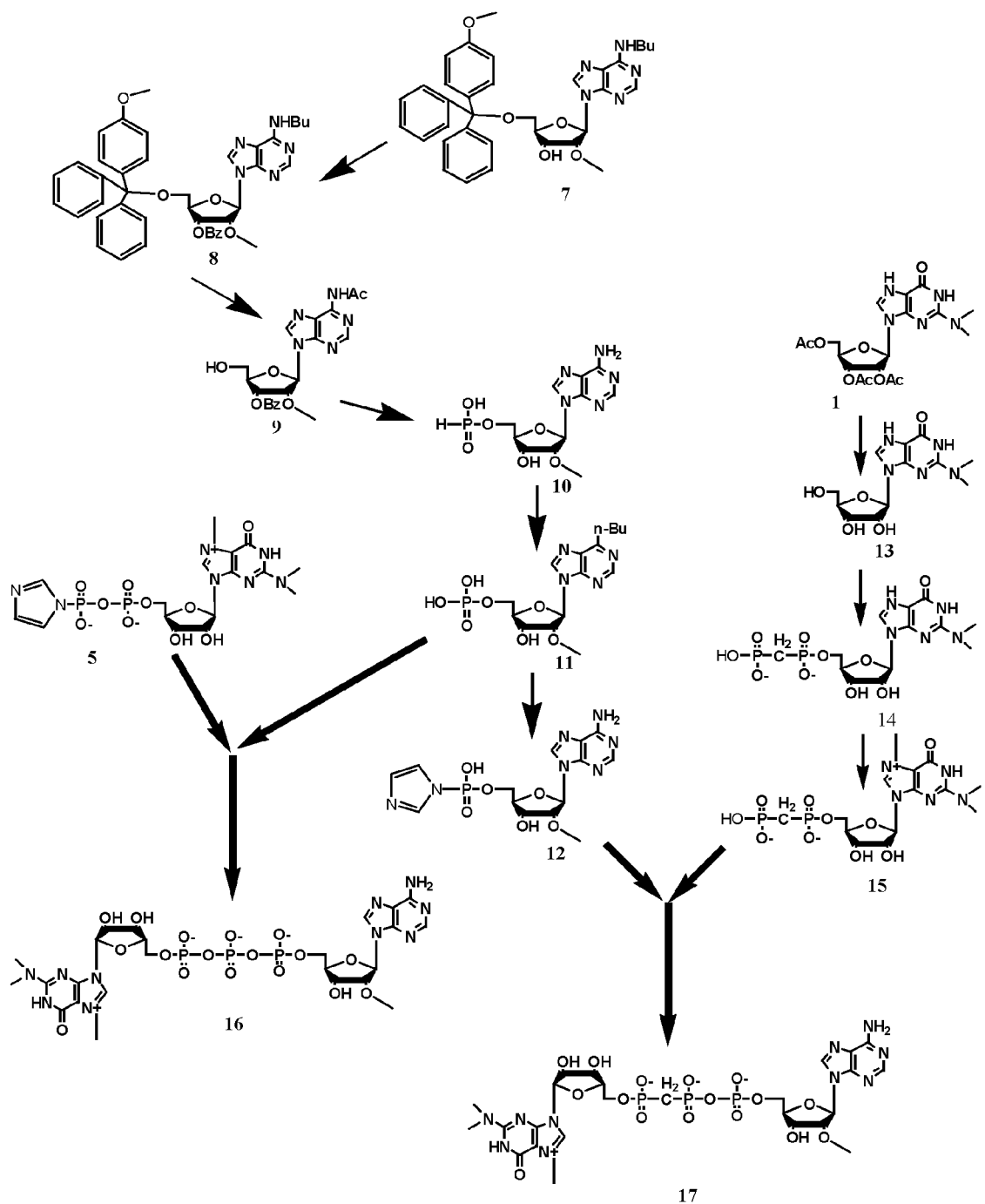

FIG. 9 shows the synthesis scheme for compounds 16 and 17.

Figure 10:

FIG. 10 highlights the difference between compounds 16 and 17.

Figure 11:
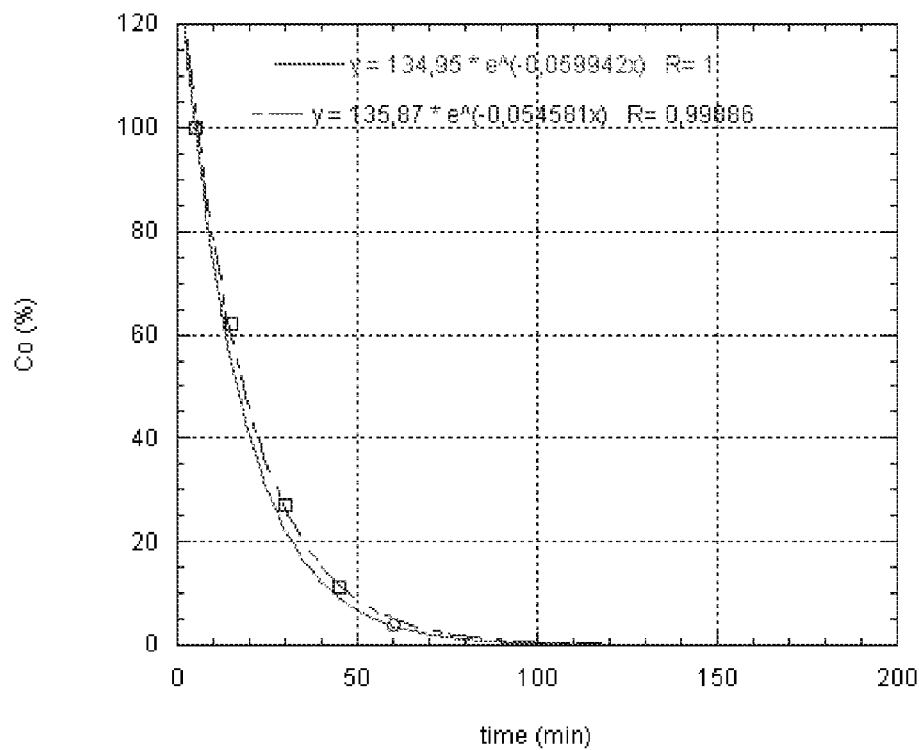

FIG. 11 shows the time dependence of the disappearance of the native m$_3$G-cap (compound 16) in cell medium with 10% serum.

Figure 12:
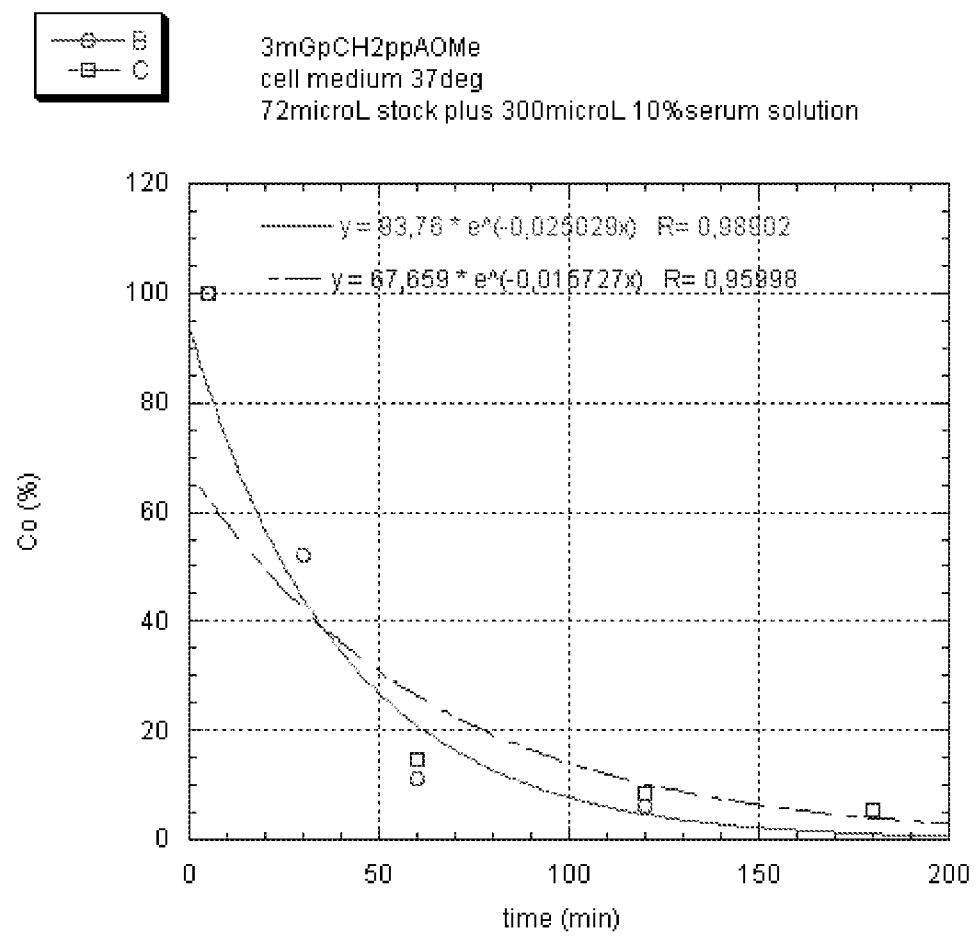

FIG. 12 shows the time dependence of the disappearance of the methylenephosphonate modified m$_3$G-cap (compound 17) in cell medium with 10% serum.

Figure 13:
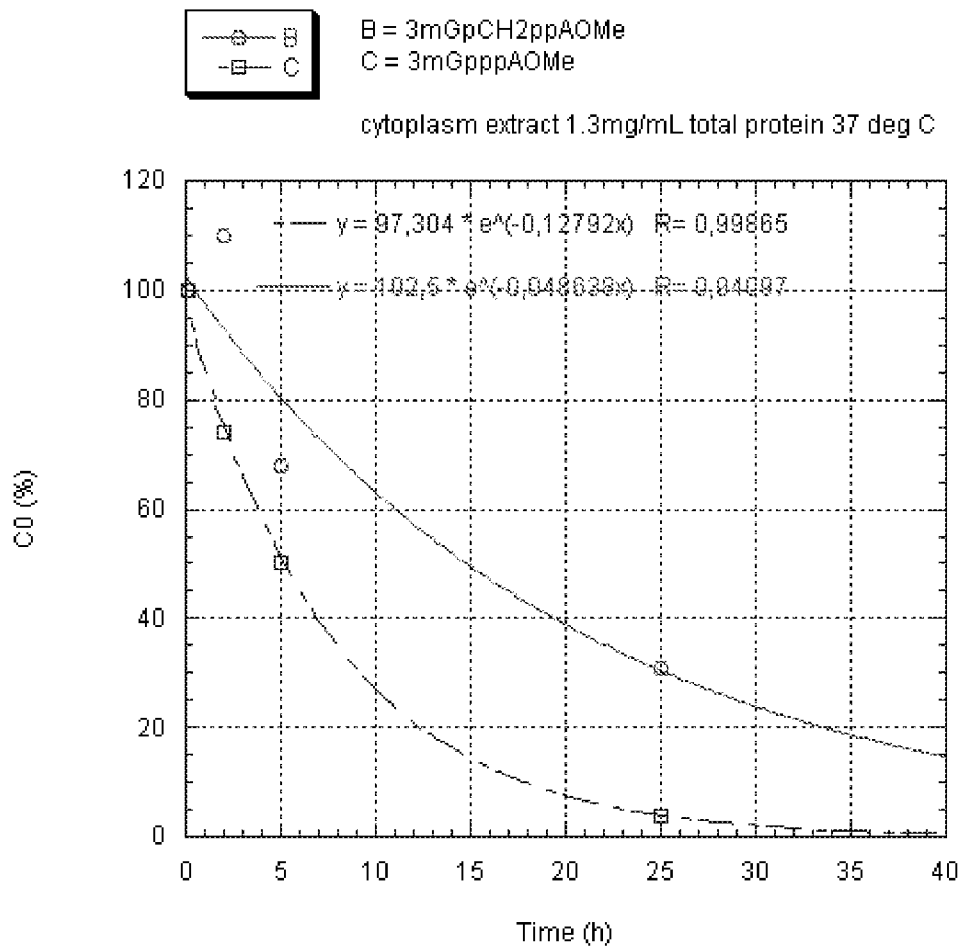

FIG. 13 shows the time dependence of the disappearance of compound 16 (squares) and 17 (circles) in cytosolic extract.

DESCRIPTION

The following description is of the best mode presently contemplated for carrying out the invention. This description is not to be taken in a limiting sense, but is made solely for the purpose of describing the general principles of the invention. The scope of the invention should be determined with reference to the claims.

Before the invention is described in detail, it is to be understood that this invention is not limited to the particular compounds described or process steps of the methods described as such compounds and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a sequence" includes more than one such sequence, and the like.

The term "analogue" is intended to encompass chemical modifications of the compounds presented, these modifications being such that can be performed by a skilled person after having obtained the information given in the present description and examples. An analogue is further defined as a compound having retained the function of the starting compound, but where the modifications convey improved properties such as increased stability, reduced immunogenicity etc.

The term "nucleic acids" here encompasses both synthetic and natural oligonucleotides and analogues, such as PNA, LNA etc, including constructs built on these components, such as siRNA and Zorro molecules, e.g. Zorro-LNA [44].

Further, the term "about" is used to indicate a deviation of +/−2% of the given value, preferably +/−5% and most preferably +/−10% of the numeric values, when applicable.

One embodiment of the invention concerns a complex for facilitating transmembrane transport of a molecular cargo into the nucleus of a mammalian cell, wherein said molecular cargo is coupled to at least one nucleic acid based nuclear localization signal. A particular feature and advantage of this embodiment is that said nuclear localization signal is a non-peptide, non-viral nucleic acid based nuclear localization signal.

Preferably said nuclear localization signal comprises 2,2, 7-trimethylguanosine CAP (m$_3$G-CAP). Said nuclear localization signal is either a natural or a synthetic m$_3$G-CAP. An example of a modified 2,2,7-trimethyl-guanosineCAP structure is specified in Formula (I) which is designed to give retained transport signal function while enhancing resistance towards degradation:

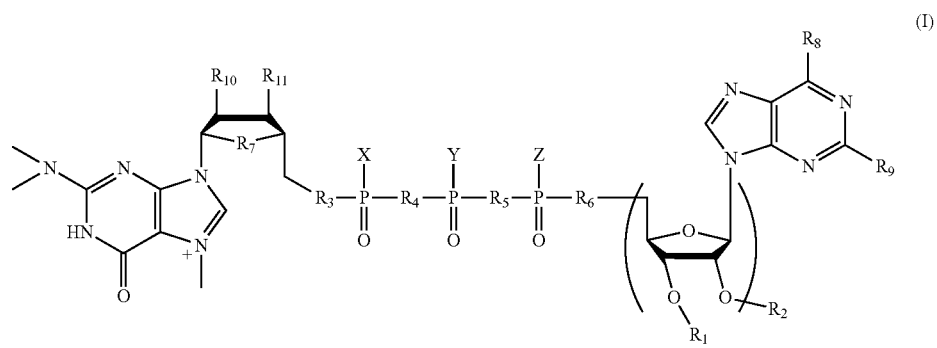

In Formula (I), $R_1$ is a cargo attached directly or a mono-, di or oligonucleotide (modified or unmodified) followed by a cargo unless the cargo is attached through $R_2$ then $R_1$ is a hydroxyl or a phosphate mono or diester;

$R_2$ is methyl or H or any unsubstituted or substituted alkyl group or is a cargo attached directly or a mono-, di or oligonucleotide (modified or unmodified) followed by a cargo;

$R_3$ is O or $CH_2$;
$R_4$ is O or $CH_2$;
$R_5$ is O or $CH_2$;
$R_6$ is O or $CH_2$;
X is OH or SH, or salts thereof;
Y is OH or SH, or salts thereof;
Z is OH or SH, or salts thereof;
$R_7$ is O, or $CH_2$;
$R_8$ is $NH_2$, H, or OH;
$R_9$ is H, $NH_2$ or OH;
$R_{10}$ is OH, or F; and
$R_{11}$ is OH, or $OCH_3$.

In the complex of Formula (I), the ribose unit in brackets is chosen from a ribose, deoxyribose, the sugar residue or sugar replacement unit of a Locked Nucleic Acid (LNA), Peptide Nucleic Acid (PNA) or any other backbone modified nucleoside unit.

According to one embodiment of the invention, both $R_4$ and $R_5$ are $CH_2$. Alternatively, $R_5$ is O when $R_4$ is $CH_2$, or $R_4$ is O when $R_5$ is $CH_2$.

It is known that phosphorothioate modification of phosphate esters as well as triphosphates can give increased resistance towards enzymatic degradation while the modified structure, although often only one stereoisomer, is still recognised by proteins/enzymes that recognise the parent structure. Synthesis of these types of modification can be done by means of methods that must be considered prior art.

Accordingly, one embodiment involves phosphorothioate modifications of the compound according to Formula I, as either isomer, i.e., with one or more of the positions X, Y and Z being SH or a salt thereof. Such modifications are performed in order to make the compound more resistant towards degradation in vivo while still recognizable by the nuclear transport system.

For similar reasons, methylenephosphonate modifications (i.e., one or more of $R_3$-$R_6$ =$CH_2$, e.g., as in example 3 and 4) can be introduced either as the sole modification or together with other modifications including those where one or more of X, Y and Z=S.

The complex can be used for transmembrane transport of any molecular cargo, such as molecules not naturally taken up by the nucleus, or only insufficiently capable of being taken up by the nucleus. According to preferred embodiments of the invention, said molecular cargo comprises a therapeutic molecule chosen among natural and synthetic peptides, proteins, oligonucleotides, morpholino oligomers or nucleic acids linked to the above structure by a covalent linkage or by non-covalent interaction.

Another embodiment of the invention is an improved method for transmembrane transport of a molecular cargo into the nucleus of a mammalian cell, wherein said molecular cargo is coupled to at least one nucleic acid based nuclear localization signal. A particular feature and advantage of this method is that said nuclear localization signal is a non-peptide, non-viral nucleic acid based nuclear localization signal.

According to an embodiment, said nuclear localization signal comprises a 2,2,7-trimethylguanosine CAP ($m_3$G-CAP) structure. According to a specific embodiment, said nuclear localization signal is either a naturally occurring or synthetic $m_3$G-CAP.

A preferred embodiment of the invention is a method for transmembrane transport of a molecular cargo into the nucleus of a mammalian cell, wherein nuclear delivery of said molecular cargo is achieved by covalent or non-covalent attachment to a modified 2,2,7-trimethylguanosine CAP structure as defined by Formula (I).

In any one of the embodiments of the inventive method, said molecular cargo comprises any molecular cargo, such as molecules not naturally taken up by the nucleus, or only insufficiently capable of being taken up by the nucleus. According to a preferred embodiment of the method, the cargo is a therapeutic molecule chosen among natural and synthetic peptides, proteins, oligonucleotides, or nucleic acids linked to the above structure by a covalent linkage or by non-covalent interaction.

Without wishing to be bound to a specific theory, the inventors believe that suitable modifications to the triphosphate function can render the $m_3$G-cap structure more resistant towards enzymatic degradation. The inventors have performed experiments in 10% serum (fetal calf serum) and cytosolic extract (HeLa cells), indicating that the tested modifications have a stabilizing effect in vivo.

Modifications of $R_4$ and $R_5$, as well as phosphorothioate modifications at the positions X, Y, and Z are contemplated, as disclosed above.

Similarly, modifications to $R_7$ (and some of the $R_{10}$, $R_{11}$ modifications) can render the $m_3$G-cap structure more resistant towards decomposition and hence enhance shelf-life, an important property of a drug delivery complex. $R_{10}$ and $R_{11}$ are also possible sites for modifications. The substituents $R_8$ and $R_9$ are intended to cover the most common purine bases, since the main interaction is stacking between the $m_3$G and this base, and both A and G can be accepted in this position.

Non-limiting examples of modified $m_3$G-caps with cargo, where the cargo is merely schematically indicated, are given below:

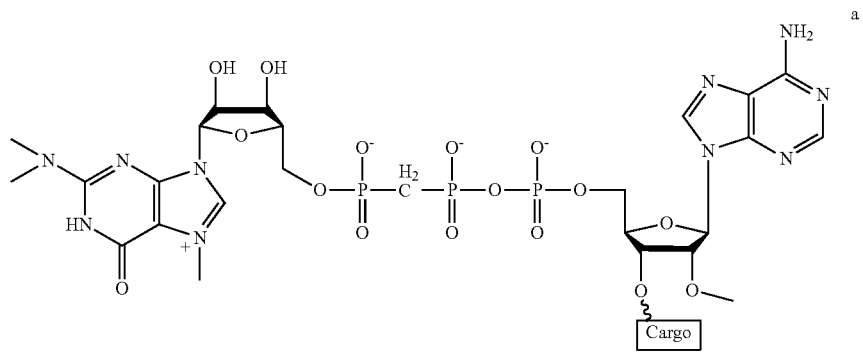

a

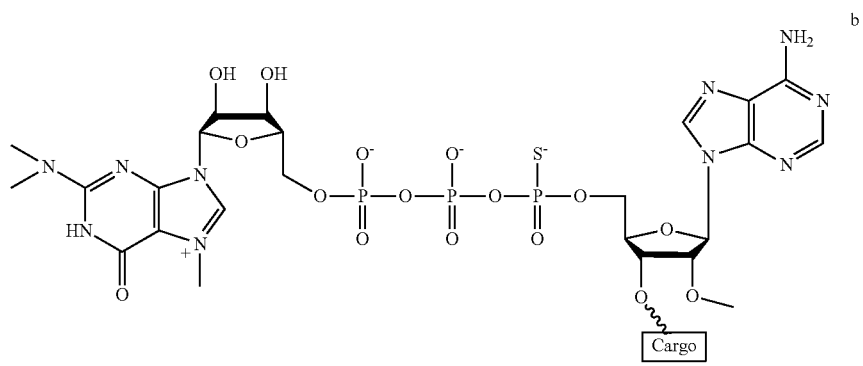
b
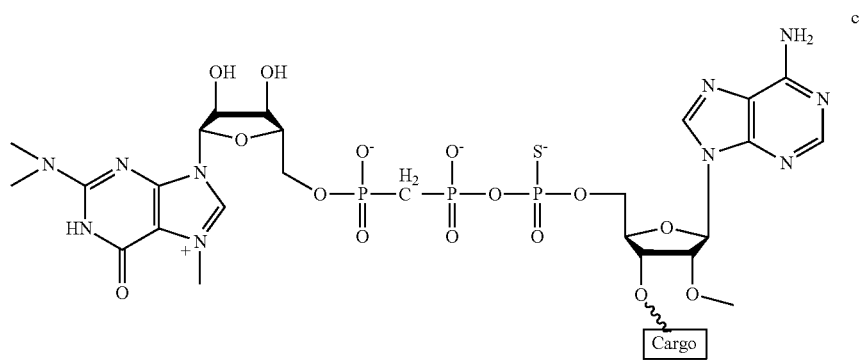
c
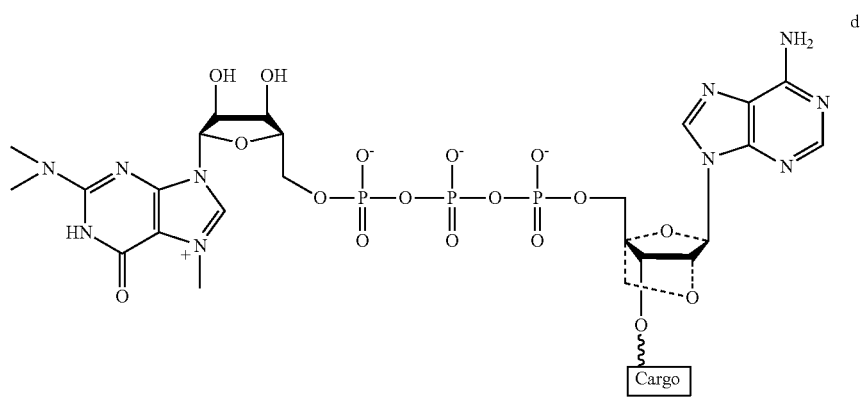
d
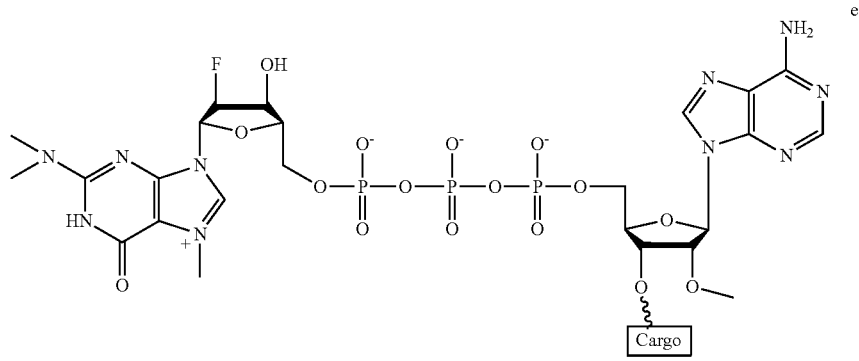
e

-continued

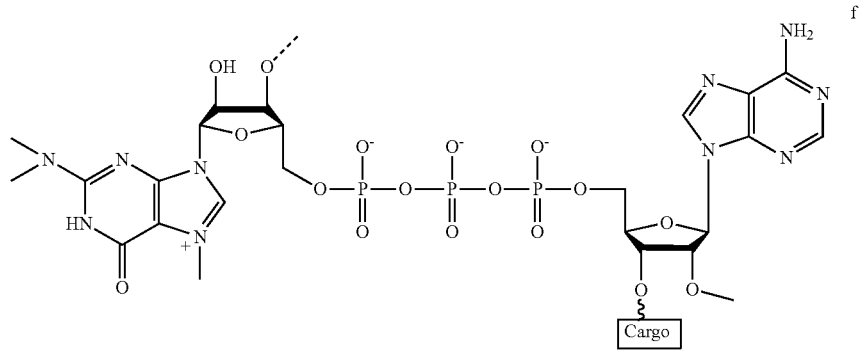

The embodiments of the invention constitute a first approach to use the U snRNA m$_3$G-CAP as an adaptor signal for the increase of nuclear transport of external cargoes such as natural and synthetic peptides, proteins, oligonucleotides, or nucleic acids.

The inventors first designed a construct composed of a fluorescent Streptavidin (STV-Alexa 488) and a defined number of RNA oligonucleotides with or without the m$_3$G-CAP at their 5' ends. The inventors initially chose the Xenopus oocyte to test their system, since the study of U snRNAs/snRNP particles has been well documented in these cells in previous experiments by others. Thus, using the Xenopus oocyte it was found that nuclear transport of the U1 snRNA species was very much dependent on the presence of the m$_3$G-cap in the RNA [18, 42]. The experiments showed that the m$_3$G-CAP was sufficient for enhancing the nuclear import of a cargo protein. More specifically, by using a defined construct with two to three m$_3$G-capped RNA oligos, which were spaced away from the cargo STV, the inventors achieved an at least 6-fold enhancement in nuclear import as compared to the uncapped counterpart.

Figure 1:
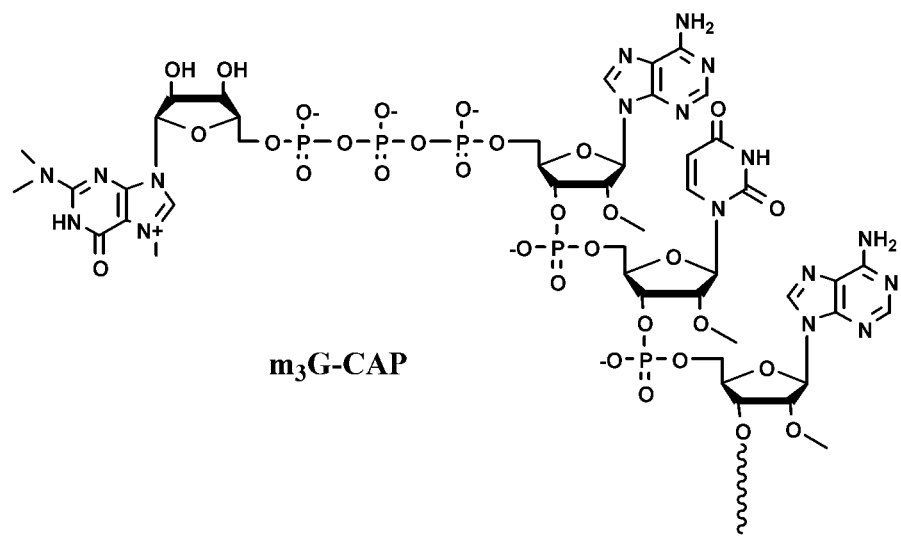
FIG. 1 illustrates the m$_3$G-CAP structure.
Figure 2:
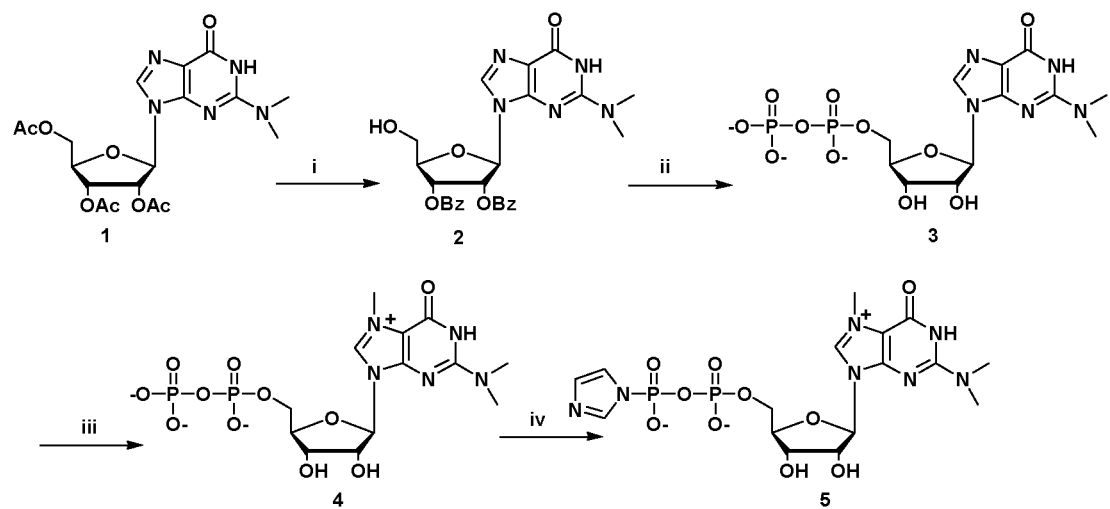
FIG. 2 shows the synthesis of m$_3$G-5'-pyrophosphorylimidazolide.

To the best knowledge of the inventors, there is only one study where the effect on nuclear import of an exogenous cargo by the m$_3$G-CAP is assessed only by conjugation of a surplus of the cap to gold labelled particles and injection of the complexes into Xenopus oocyte cytoplasm [45]. While these authors state on page 369 that they " . . . found that the m$_3$g-cap signal alone is sufficient for the nuclear import of the gold-m$_3$g-cap (FIG. 2A).", this statement does not seem to be substantiated by the corresponding results. Thus, there is no data presented from a control group lacking the m$_3$g-cap making it impossible to estimate the effect of the m$_3$g-cap, and more importantly, in FIG. 2A there is not a single indicated gold particle in the nucleus (while there are 3 in the cytoplasm). Based on [45] it seems as if that the addition of recombinant snurportin enhances the nuclear uptake, but this is outside the scope of the current invention. Moreover, in the present study, to emphasise the possibility that the cap can be used as a specific adaptor signal, the inventors constructed the cargo-cap complexes to have a defined number of m$_3$G-CAP structures (which is not possible to assess with the direct conjugation of the m$_3$G-CAP to gold particles). On top of that, the particles are also different in the way that the m$_3$G-CAP is sitting on a short oligonucleotide that is bound to a STV through the use of a relatively long spacer (here 34 atoms long) with biotin at its end (see FIG. 5) which shows that the cargo can be spaced away from the import complex formed by the m$_3$G and the import receptors.

To further test the concept, the inventors used a novel system where they performed a nuclear import assay in live mammalian cells by using a protein delivery reagent that is able to release the cargo into the cytosol of cells. This system resembles the pathways taken by molecules in gene delivery protocols, so it is believed to be relevant in assessing the properties of the m$_3$G-CAP for future uses in the gene delivery field. Also in this case the m$_3$G signal was able to direct nuclear translocation of the cargo quite efficiently.

As a proof of concept for the application of this nuclear import strategy in a therapeutic protocol, the inventors used a splice correction assay where antisense oligonucleotides are employed to correct a malfunctioning splice occurring due to a mutation in the beta-globin intron. By using antisense oligonucleotides with an incorporated m$_3$G-CAP structure an increased splice correction was achieved, measured by increase of activity of a Luciferase reporter construct. The delivery of simple single-stranded oligonucleotides to nucleus of cells and especially dividing cells should be a very useful embodiment of the invention. Consequently the inventors postulate that only by using either very minimal concentrations of oligonucleotide during the transfection procedure or less efficient oligonucleotides it is possible to see effect of a nuclear targeting system. The reasoning is that if the cell is flooded with a high concentration of oligonucleotide, it will rapidly equilibrate between the cytoplasm and nucleus and will quickly achieve a very high local nuclear concentration. In contrast, by using suboptimal conditions, the oligonucleotide concentration achieved in the nucleus might not be sufficient for an efficient splice correction activity. In this case having a nuclear targeting moiety in the oligonucleotide can help to increase local nuclear concentrations by redirecting oligonucleotides diffusing out of the nucleus. However, an additional factor that could be influencing the activity of the m$_3$G-capped oligonucleotides cannot be excluded, which is a possible localization of these oligonucleotides into specific splice regions, since the m$_3$G-CAP is naturally present in U snRNPs that are targeted to splice compartments of the nucleus. Therefore, the complex and method of the invention are believed to be particularly advantageous. A possible area of use is gene silencing using bifunctional oligonucleotides, so called U1 adaptors, binding to the U1 small nuclear RNA component of the U1 snRNP splicing factor.

Splice correction is a promising treatment strategy, currently used e.g. in experimental treatments for Duchenne Muscular Dystrophy with the aim of converting this severe form of muscle disease into the more mild form called Becker disease (these patients lack the inclusion of certain exons, while they maintain the reading-frame). Altering splicing could also result in many other effects such as inducing forms of proteins causing apoptosis in e.g. tumour cells, by converting one splice-form into another, or removing un-natural exons formed by mutations.

Other forms of oligonucleotides that could be transported using a complex according to the present invention are siRNA (short interfering RNA) modulating chromatin as well as anti-sense oligonucleotides and triplex-forming oligonucleotides. Another category includes so-called Zorro molecules, such as Zorro-LNA. For more details on the construction and uses of Zorro-LNA, see Rongbin Ge et al. [46] incorporated herein by reference.

The invention is also applicable to other methods and therapies involving RNA interference, where the complex and method can be used to introduce RNAi or siRNA molecules to the desired location in the cell.

In addition to splice correction, discussed above, also the possibility of disturbing or preventing the normal splice is contemplated. This can be termed "splice corruption" and is an approach where a transcript necessary for survival of the cells is disturbed or destroyed. This could be a promising approach against tumour cells.

In any of the above applications, and others near at hand to a skilled person, the complex and method according to the invention offers an advantage in that effective and targeted transmembrane delivery makes it possible to reduce the amount of therapeutic substance administered to the patient. This is favourable as it reduces the cost for synthesizing the therapeutic substance, e.g. an oligonucleotide or the like. Another advantage is the reduction of the risk for side-effects, a particular consideration when life-long treatments of chronic diseases is contemplated, e.g. Duchenne Muscular Dystrophy.

The initial experiments performed by the inventors clearly show the capabilities of an $m_3$G-capped oligonucleotide in directing nuclear translocation of a cargo molecule in different assay systems. Consequently this is believed to be the preponderant mechanism for the increased activity, in the conditions of the tested system, of the $m_3$G-capped antisense oligonucleotides.

In terms of development of new vector-based systems for nuclear targeting, the inventors believe that the use of a signal that is naturally present in endogenous RNA molecules can have potential advantages over some methods based on association of very positively charged NLS peptides with nucleic acids. These peptides can interact unspecifically by electrostatic interactions with the nucleic acids with possible implications in the recognition of the NLS by the import receptors (hampered recognition of the NLS signal by the import receptors) making it difficult to control the properties of the nucleic acid-NLS complex and to assess what is their actual mechanism in transfection protocols.

The complex and method as disclosed in the description and claims have many advantages. Surprisingly, the modified $m_3$G-Cap has shown to be easier to synthesize that the natural form. Further, the modified $m_3$G-Cap is 5' selective, which is an advantage when coupling it to a molecular cargo, or linker. Various linkers can be used, including nucleic acid based linkers, where "nucleic acids" include both natural and synthetic oligonucleotides and their analogues such as PNA, LNA etc.

The invention as defined in the claims includes the use of at least one $m_3$G-Cap, but it is contemplated, depending on the size and properties of the cargo, that more than one localization signal or $m_3$G-Cap is attached to the cargo. A lager cargo can be covalently or non-covalently linked to 1, 2, 3, 4 or more localization signals. It is envisioned that a combination of localization signals, including but not limited to $m_3$G-Cap like structures, can be used.

The inventors have also shown that the complex has the potential of handling molecules of highly varying sizes. The examples using on the one hand an antisense oligonucleotide, and on the other hand streptavidin, show that the invention is applicable to any cargo ranging from short oligonucleotides to large biomolecules, at least equal in size to streptavidin, or about 60 kDa.

EXAMPLES

Example 1

Synthesis and In Vitro Tests

The inventors synthesized a compound according to the invention, and showed that $m_3$G-capped RNA oligonucleotides are able to direct nuclear accumulation of a cargo protein (fluorescent Streptavidin) in *Xenopus* oocytes, and in a mammalian cell line. The inventors also showed that $m_3$G-capped 2'-O-Methyl RNA antisense oligonucleotides have increased efficiency in a splice correction assay using HeLa/Luc705 cells.

Material and Methods

Reagents and solvents, Acetonitrile (HPLC grade, Merck), Dichloromethane (Fisher Scientific, Analytical Grade), were of commercial grade and used as received except DMF and pyridine (both from Merck) that were dried over 4 A molecular sieves. Silica gel column chromatography were performed on Merck G60, TLC-analysis was carried out on pre-coated Silica Gel 60 $F_{254}$ (Merck), with detection by UV light. NMR spectra were recorded on a Bruker AVANCE DRX-400 instrument (400.13 MHz for $^1$H, 162.00 MHz for $^{31}$P, 100.62 MHz for $^{13}$C). Reverse phase and ion exchange HPLC was carried out on a Jasco HPLC system using the following columns: analytical Reprosil-Pur C18-AQ (250×3 mm) at 1 mL/min flow rate, preparative Reprosil-Pur C18-AQ (250×20 mm) at 10 mL/min flow rate, or Dionex Nucleo-Pac PA-100 (4×250 mm) at 1 mL/min flow rate. Buffers for reverse phase chromatography (Reprosil columns) were: A, 50 mM TEAA pH 6.5, B, 50 mM TEAA pH 6.5 in 50% $CH_3CN$. Buffers for ion exchange chromatography (Dionex column) were: A, 20 mM NaOAc in 30% $CH_3CN$, B, 0.3 M $LiOClO_4$, 20 mM NaOAc in 30% $CH_3CN$. Mass spectra (TOF-MS, ES) were obtained by using a Micromass LCT electrospray time-of-flight (ES-TOF) instrument and the MAXENT program for calculation of masses from multiply charged ions. The non-capped oligonucleotides were purchased from Fidelity Systems Inc. of Gaithersburg, Md., USA (PM02-p) and Eurogentech of Seraing, Belgium (AS705-p) and reconstituted in nuclease free water (Qiagen). AS705-p and PMO2-p were converted to the $m_3$G-capped derivatives $m_3$G-CAP-AS705 and $m_3$G-CAP-PMO2 by reaction with the $m_3$G-5'-pyrophosphorylimidazolide 5 in a Mn(II) catalysed capping reaction [32]. Synthesis of the $m_3$G 5'-pyrophosphateimidazolide 5, was modified compared to previously published procedures [32, 33] in order to simplify larger scale synthesis. The 5'-Pyrophosphate 3 was synthesised in a new one-pot, five-step synthesis, based on reported reactions [34-37]. See FIG. 2.

TABLE 1

Oligonucleotides

| Name | Sequence |
|---|---|
| p-AS705<br>(oligo p1) | - pAUACCUCUUACCUCAGUUACA<br>p = phosphate group<br>AUA = U snRNA common 5' end cap sequence<br>N = 2'-O-methyl RNA bases |
| m₃G-CAP-AS705<br>(oligo Cp1) | - m₃GpppAUACCUCUUACCUCAGUUACA<br>p = phosphate group<br>AUA = U snRNA common 5' end cap sequence<br>m₃G = 2,2,7-trimethyl Guanosine CAP<br>N = 2'-O-methyl RNA bases |
| p-AS705scr<br>(oligo p2) | - pAUAACUACCCGAUAUCUCCUC |
| m₃G-CAP-AS705scr<br>(oligo Cp2) | - m₃GpppAUAACUACCCGAUAUCUCCUC |
| p-PM02<br>(oligo2) | - pAUAAGAGA-L-b<br>p = phosphate group<br>L = 34 atom linker<br>b = biotin<br>N = 2'-O-methyl RNA bases |
| m₃G-CAP-PM02<br>(oligo2CAP) | - m₃GpppAUAAGAGA-L-b<br>L = 34 atom linker (see below)<br>b = biotin (see below)<br>m₃G = 2,2,7-trimethyl Guanosine CAP<br>N = 2'-O-methyl RNA bases |

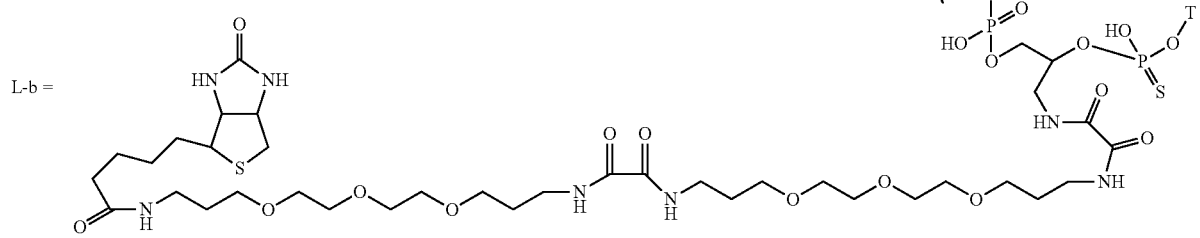

L-b =

Synthesis of 1',2'-O-dibenzoyl-N², N²,-dimethylguanosine 2 a: Compound 1 (1.5 g, 3.4 mmol) was dissolved in pyridine (2 mL) and aqueous ammonia was added. The reaction was stirred at room temperature for 3 h until TLC showed full deprotection. Solvents were evaporated to dryness and the compound was recrystallised from water. Yield 0.68 g, 65%. $^1$H NMR (DMSO d$_6$) δ 3.06 (6H, s, NMe$_2$), 3.48-3.63 (2H, m, 5'-CH$_2$), 3.86 (1H, q, J=4 Hz, H$^{4'}$), 4.11 (1H, q, J=4 Hz, H$^{3'}$), 4.50 (1H, q, J=4 Hz, H$^{2'}$), 4.91 (1H, t, J=5.4 Hz, OH$^{5'}$) 5.15 (1H, d, J=4.8 Hz, OH$^{3'}$), 5.38 (1H, d, J=6.1 Hz, OH$^{2'}$), 5.71 (1H, d, J=5.8 Hz, H$^{1'}$), 5.92 (1H, s, H8), 10.69 (1H, bs, NH), $^{13}$C NMR δ 38.1 (NMe$_2$), 61.8 (C$^{5'}$), 70.7 (C$^{3'}$), 73.7 (C$^{2'}$), 85.4 (C$^{4'}$), 87.0 (C$^{1'}$), 100.0, 116.4, 136.8 (C$^8$), 151.1, 153.3, 157.7, MS (ES-TOF) m/z calculated: 312.13. found: 312.54.

b: The deprotected compound (4.8 g, 15.4 mmol) was dried by evaporation of added dry DMF (2×), suspended in a 1:1 mixture of DMF and Py (150 mL) whereupon monomethoxytrityl chloride was added (1.1 eq, 16.9 mmol, 5.2 g). The reaction was left stirring at room temperature for 48 h. Water was added to the reaction mixture and the product was extracted with dichloromethane. The organic layer was separated, dried over anhydrous MgSO$_4$, filtered and concentrated under reduced pressure. DMF was removed by co-evaporation with toluene, and finally with dichloromethane. The product 5'-monometoxytrityl N,N-dimethylguanosine was purified on column chromatography using a linear gradient of MeOH in dichloromethane (0-20%). Yield 5.6 g, 63%. $^1$H NMR (CDCl$_3$/CD$_3$OD) δ 2.99 (6H, s, NMe$_2$), 3.28 (2H, m, 5'-CH$_2$), 3.70 (6H, s, OMe×2), 4.17 (1H, q, J=4.1 Hz, H$^{4'}$), 4.28 (1H, t, J=5.3 Hz, H$^{3'}$), 4.59 (1H, t, J=4.9 Hz, H$^{2'}$), 5.79 (1H, d, J=5.4 Hz, H$^{1'}$), 7.11-7.31 (14H, m, MMTr), 7.6 (1H, s, H8), $^{13}$C NMR δ 46.2 (NMe$_2$), 64.0 (OMe), 72.2 (5'-CH$_2$), 79.1 (C$^{3'}$), 82.2 (C$^{2'}$), 92.1 (C$^{4'}$), 95.5 (C$^{1'}$), 120.0, 127.0, 128.3, 130.4, 144 (C$^8$), 210.0, 227.0, 229.0. MS (ES-TOF) m/z calculated: 582.24. found: 582.12.

c: 5'-Monometoxytrityl N,N-dimethylguanosine (5.6 g, 9.6 mmol) was dried by evaporation of added dry pyridine (2×), dissolved in the same solvent (100 mL) and put on an ice-bath. Benzoyl chloride (2.2 eq, 2.44 mL, 21.1 mmol) was added dropwise and after 5 min the reaction was taken off the ice-bath and then stirred at room temperature overnight. A saturated aqueous solution of NaHCO$_3$ was then added and the solvent was evaporated under reduced pressure. The crude product was dissolved in dichloromethane and washed with a saturated aqueous solution of NaHCO$_3$ (2×). The organic layer was separated, dried over anhydrous MgSO$_4$, filtered and concentrated under reduced pressure. Traces of pyridine were removed by co-evaporation with toluene (3×) and dichloromethane (2×).

d: The crude product was deprotected by dissolving it in 80% acetic acid (100 mL) at room temperature. After 5 h the acetic acid was evaporated and traces of acid was removed by co-evaporation with toluene (3×) and dichloromethane (1×): The product was purified by column chromatography using a linear gradient of methanol in dichloromethane (0-20%). Yield 4.2 g, 84%. $^1$H NMR (CDCl$_3$) δ 3.27 (6H, s, NMe$_2$), 4.02 (2H, m, 5'-CH$_2$), 4.51 (1H, bs, H4'), 6.06 (1H, dd, J=3.4 Hz, H$^{3'}$), 6.13 (1H, d, J=6.4 Hz, H$^{1'}$), 6.57 (1H, t, J=6.1 Hz, H$^{2'}$), 7.32-7.42 (6H, m, 2Bz), 7.69 (1H, s, H$^8$), 7.89-7.99 (4H, m, 2Bz). $^{13}$C NMR δ 38.9 (NMe$_2$), 62.3 (5'-CH$_2$), 72.3 (C$^{3'}$), 72.7 (C$^{2'}$) 84.4 (C$^{4'}$), 88.0 (C$^{1'}$), 117.9, 128.6, 128.7, 129.2, 129.9, 133.8 (C$^8$), 137.9, 151.4, 153.4, 158.9, 165.0, 165.6. MS (ES-TOF) m/z calculated: 520.18. found: 520.27.

Synthesis of N$^2$,N$^2$,-dimethylguanosine 5'-pyrophosphate 3

To compound 2 (171 mg, 0.33 mmol) in 2 mL of dry DMF was added salicyl chlorophosphite (1.9 eq, 0.126 g, 0.627 mmol) and the reaction mixture was stirred at room temperature under argon atmosphere. After 15 min a solution of tetra(tri-n-butylamine)pyrophosphate in DMF (2 eq, 0.66 mmol, 1.32 mL from 0.5 mM stock$^\#$, which was vortexed with 0.5 mL tri-n-butylamine directly before reaction) was added. After 20 min a solution of iodine (0.091 g, 1.1 eq, 0.363 mmol) in 1.5 mL pyridine, containing water (0.33 mmol, 0.006 mL, 1 eq) was added. After an additional 15 min ethylenediamine (0.11 mL, 1.65 mmol, 5 eq) was added and the reaction was stirred for 1 h. Solvents were evaporated and the crude product was dissolved in NH$_3$(aq) and left to react overnight. After concentration was the crude product dissolved in water and purified by preparative RP HPLC using a gradient of buffer B in buffer A (0-20% B over 30 min) concentration of collected fractions gave compound 3 as the tris(triethylamine)salt. RT=23 min. Yield 55.8 mg, 22% (after five steps). $^1$H NMR (D$_2$O) δ 1.27 (27H, t, J=7.2 Hz, 3×Et$_3$N), 3.17 (6H, s, NMe$_2$), 3.21 (18H, q, J=7.2 Hz, 3×Et$_3$N), 4.20 (2H, m, 5'-CH$_2$), 4.34 (1H, bs, H4'), 4.39 (1H, bs, H$^{3'}$), 4.80 (1H, H$^{2'}$+H$_2$O), 6.02 (1H, d, J=5.9 Hz, H$^{1'}$), 8.10 (1H, s, H$^8$), $^{31}$P NMR δ –8.5, –9.9. MS (ES-TOF) m/z calculated: 470.05. found: 470.18. $^\#$[0.5 mM stock solution: sodium pyrophosphate (2.23 g, 5 mmol) was dissolved in H$_2$O and applied to a column of Dowex 50WX8 in the H$^+$ form, and the column was washed with water. The eluate was directly dropped to cooled solution of tri-n-buthylammine (2.38 mL, 10 mmol) in ethanol (20 mL). The column was washed until the eluate pH increased to 5. The ethanol water solution was evaporated to dryness and co-evaporated (2×) with ethanol and finally with anhydrous DMF. The residue was dissolved in DMF and finally diluted to 10 mL with anhydrous DMF giving 0.5 mM stock solution, which was kept over 4 A molecular sieves.]

Synthesis of N$^7$,N$^2$,N$^2$-trimethylguanosine 5'-pyrophosphate 4

Compound 3 as the tris(triethylammonium) salt (50 mg, 0.064 mmol) was dissolved in dry DMF (1 mL) and methyl iodide was added (0.08 mL, 1.28 mmol, 20 eq). The reaction was stirred at 40° C. for 5 h. The solvent was evaporated and the product dissolved in water and purified by preparative RP-HPLC using a gradient of buffer B in buffer A (0-10% B over 40 min). Evaporation of collected fractions gave compound 4 as the tris(triethylammine)salt. RT=37.2 min. Yield 12.5 mg, 25%. $^{31}$P-NMR (D2O): δ =5.9 and 9.6 ppm. MS (ES-TOF) m/z calculated: 484.08. found: 484.12.

Synthesis of N$^7$,N$^2$,N$^2$,-trimethylguanosine 5'-pyrophosphorylimidazolide 5

Compound 4 (12.5 mg, 0.0158 mmol) was dissolved in DMF (1.6 mL) containing triethylamine (0.08 mL) and was kept stirring at room temperature. To the mixture was added imidazole (12.9 mg, 0.19 mmol, 12 eq), followed by triphenylphosphine (49 mg, 0.189 mmol, 12 eq) and di-2-pyridyldisulfide (41.5 mg, 0.189 mmol, 12 eq). The reaction was stirred at room temperature for 24 h. After that time the solvent was evaporated under reduced pressure and the crude product was dissolved in water and purified by RP-HPLC (analytical system set up) using a gradient of buffer B in buffer A (0-20% of B over 30 min). Evaporation of collected fractions gave compound 5 as the tris(triethylammine)salt. RT=22.4 min. Yield 2.5 mg, 19%. MS (ES-TOF) m/z calculated: 534.0903. found: 534.0927.

Figure 3:
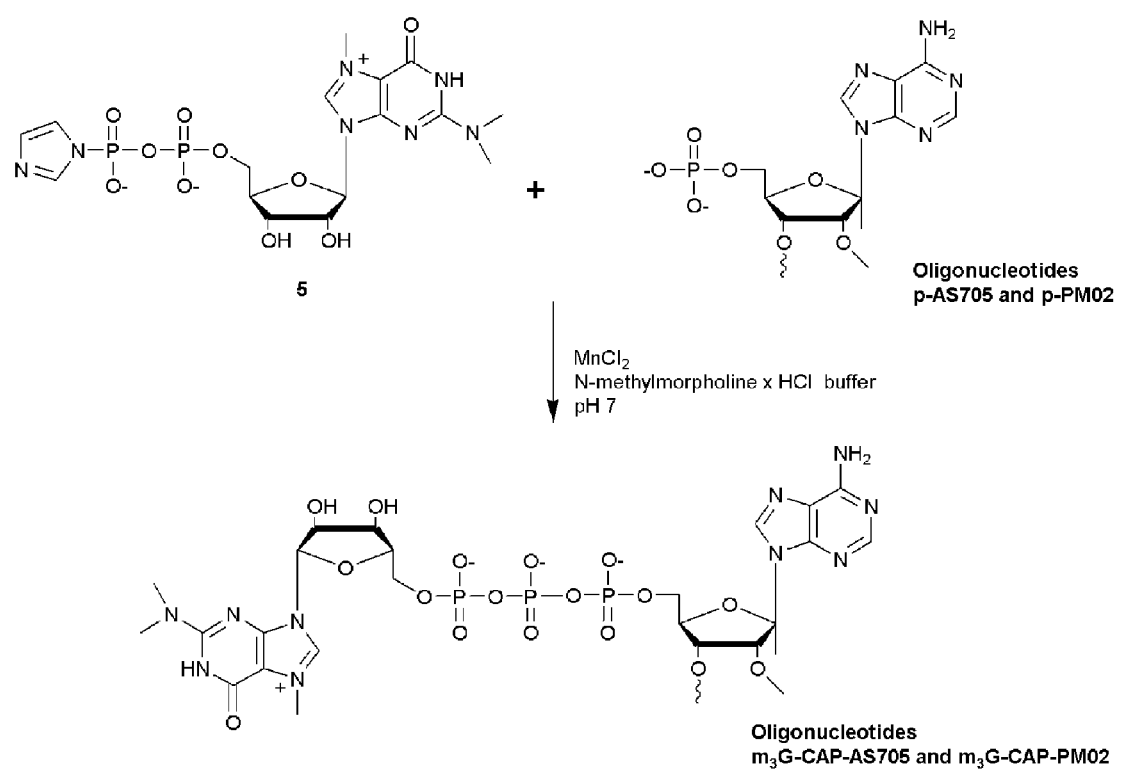
FIG. 3 shows the reaction scheme for attachment of the m$_3$G-CAP to oligonucleotides, also called the capping reaction.
Figure 4:
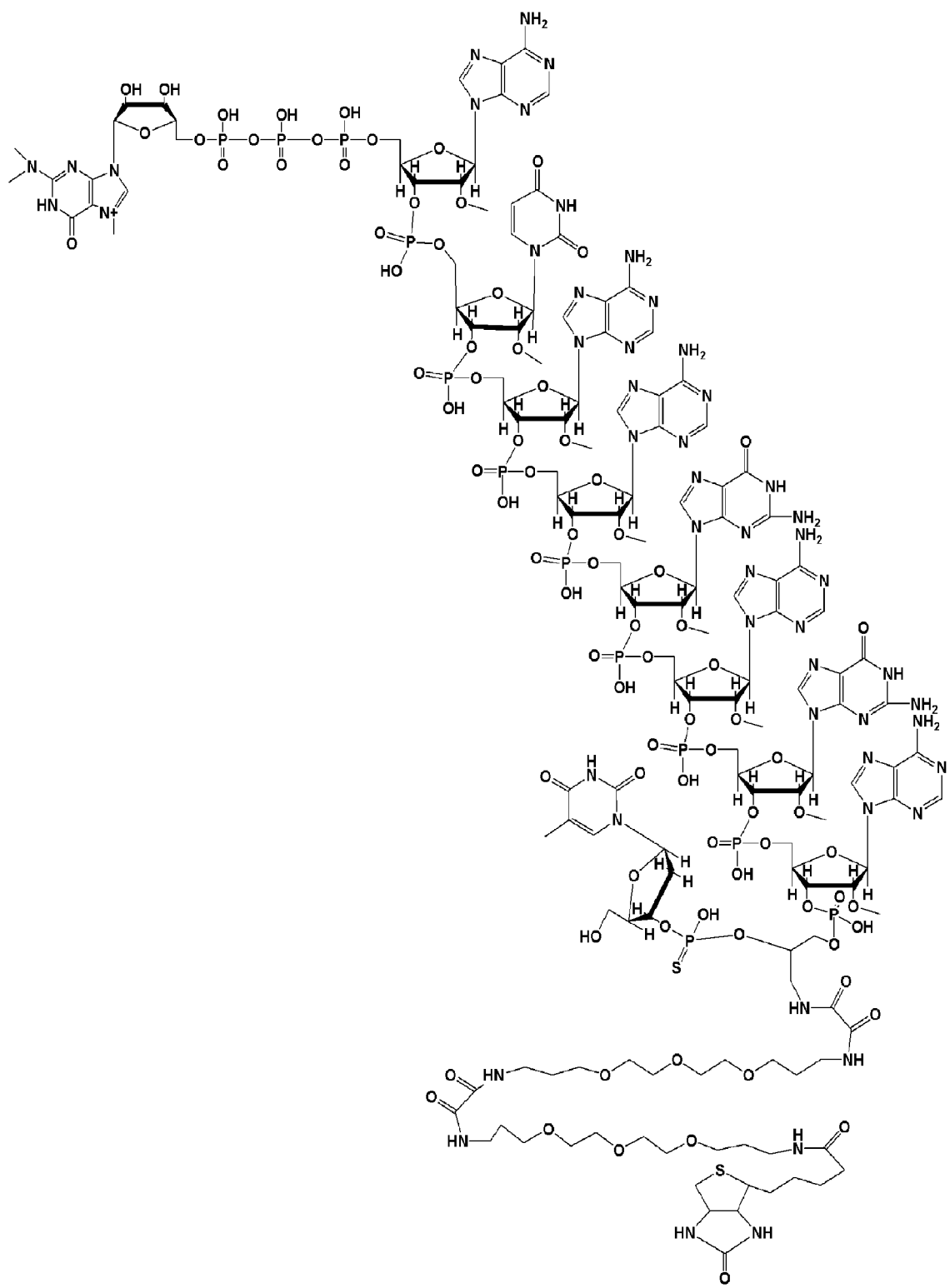
FIG. 4 shows the structure of the m$_3$G-CAP-PMO2 oligonucleotide.

Procedures for Capping Reactions with Oligonucleotides AS705-p and PMO2-p (The reaction scheme or attachment of the m$_3$G-CAP to oligonucleotides is shown in FIG. 3).

a) Pyrophosphorylimidazolide 5 (725 nmol, 0.543 mg, 10 eq) was dissolved in 0.1 mL of 0.2 M N-methylmorpholine.HCl buffer pH 7.0, containing MnCl$_2$ (10 eq in 0.1 mL) and added to lyophilized oligonucleotide AS705-p (15OD at 260 nm, 72.5 nmol). The reaction mixture was kept at 30° C. for 7 days after which it was treated with EDTA solution (0.1 M, 0.005 mL) and analyzed by reverse phase HPLC. The capped product m$_3$G-CAP-AS705 was purified by RP-HPLC using a linear gradient of Buffer B in buffer A (0-35% B over 40 min), RT=38.8 min MS (ES-TOF) m/z calculated: 7379, observed: 7379.

b) Pyrophosphorylimidazolide 5 (680 nmol, 0.51 mg, 10 eq) was dissolved in 0.1 mL of 0.2 M N-methylmorpholine-.HCl buffer pH 7.0, containing MnCl$_2$ (10 eq in 0.1 mL) and added to lyophilized oligonucleotide PMO2-p (7OD at 260 nm, 68 nmol). The reaction mixture was kept at 30° C. for 7 days after which it was treated with EDTA solution (0.1 M, 0.005 mL) and analyzed by ion-exchange HPLC. The capped product m$_3$G-CAP-PMO2 was purified by IE HPLC using a linear gradient of buffer B in buffer A (0-27% B over 40 min), RT=36.0 min, and after evaporation of the solvent the product was desalted by RP-HPLC using a linear gradient of buffer B in buffer A (0-60% B over 40 min), MS (ES-TOF) m/z calculated: 4487, observed 4487.

Cell Culture

U2OS cell line was obtained from American Type Culture Collection (ATCC; HTB-96, Rockville, Md., USA) and the HeLa/Luc705 [38] comes originally from Dr. R Kolle (University of North Carolina at Chapel Hill). Cells were cultured in Dulbecco's modified eagle medium (DMEM) supplemented with 10% (v/v) heat inactivated fetal calf serum (Invitrogen) in a 37° C. humidified 5% CO$_2$ incubator.

Oocyte Microinjections & Western Blot Analysis

Streptavidin-Alexa488 (Molecular Probes)+oligonucleotide constructs (FIG. 5) were formed by incubating 3 μg STV (Streptavidin) reconstituted in 1× phosphate buffered saline (PBS, pH 7.4) with 2-4 times molar amount of biotinylated oligonucleotide constructs. The volume was adjusted with nuclease free water (Qiagen) to have a final concentration of 329 ng STV/μl and the incubation proceeded for 2 h at room temperature and if not used the same day the constructs were stored at 4° C.

*Xenopus laevis* oocytes stage IV-V were prepared and collagenised as follows: a lobe of the frog ovary, about 2-3 ml volume, was minced with a pair of scissors in ORs buffer and then digested with 7 U of a preparation of purified collagenase (Liberase Blendzyme 3, Roche) for 2-2.5 Hrs at 19° C. during gentle agitation. The collagenase treatment is discontinued when the lobes of connected oocytes have been dispersed into individual oocytes. The oocytes are then rinsed in OR2 (82 mM NaCl; 2.5 mM KCl; 1 mM Na2HPO4; 5 mM HEPES pH 7.8; 1 mM MgCl; 1 mM CaCl) and stored at 19° C. in OR2 buffer with 10 μg Gentamicin/ml (SIGMA).

Prior to microinjections the prepared STV-oligo constructs were spun down at 16,000×g for 5 minutes. A volume of 41.4 nl of STV-oligo constructs was injected in the cytoplasm of the oocyte using the Nanoinjector 2000™ pump (World Precision Instruments, Inc) followed by incubation at 19° C. in OR2 buffer for 4 h.

After incubation, oocyte nuclei were manually dissected in nuclear dissection buffer (140 mM KCl; 0.5 mM $MgSO_4$; 20 mM Tris-HCl pH 7.2) and collected directly in 2× Laemelli sample buffer.

Collected nuclei were boiled for 5 min and nuclear protein lysates were resolved in a 4-12% NuPAGE Bis-Tris gel (Invitrogen) and transferred to PVDF membrane. After transfer SDS-PAGE gel and PVDF membrane were stained by PAGE blue protein staining solution (Fermentas) and Ponceau S (Sigma-Aldrich) respectively, as controls for protein loading. The PVDF membrane was then blocked with blocking solution (5% milk in PBS 0.1% Tween) and probed with 1:50,000 dilution of goat anti-STV antibody (Abcam, Cambridge, UK) followed by rabbit anti-goat IgG conjugated to horseradish peroxidase (1:2000 dilution). Visualization was performed by chemiluminescence with SuperSignal West Pico Chemiluminescence Substrate (Pierce, Rockford, Ill., USA).). Quantification of western blot results was done by densitometry using a Fluor-S MultiImager and the Quantity One® software (Bio-Rad).

For the fluorescent microscopy imaging, the same injection conditions described before were used but after 4 h-6 h incubation at 19° C. in OR2 buffer the nuclei were manually dissected out in nuclear dissection buffer and immediately imaged. Visible light and fluorescent photos were taken with the use of a Stereo microscope Leica MZ6 equipped with a Leica stereo fluorescent module and a Leica Video/photo tube to which was attached a Canon powershot S40 Camera. Photos were captured using the program Canon remote capture version 2.5.1.11.

Streptavidin-Oligo Complex Transfections

U2OS cells were seeded on top of coverslips in a 24-well plate with DMEM+10% FCS the day before transfection so that they were confluent or close to confluency the next day.

Streptavidin-Alexa488 (Molecular Probes)+oligonucleotide constructs (FIG. 5) were formed by incubating 2 μg STV (Streptavidin) reconstituted in 1×PBS buffer (pH 7.4) with 2-4 times molar amount of biotinylated oligonucleotide constructs for 2 h at room temperature 20 mM Hepes buffer (pH 7.4) was then used to bring the total volume up to 100 μl and then 3.5 μl of PULSin transfection reagent (PolyPlus-Transfection, New York, USA) was added. The mixture was vortexed and left to incubate for 15 min at room temperature. During this incubation time the cells were washed twice with PBS and 900 μl of pre-warmed OPTImem (Invitrogen) was added to the wells. The PULSin complexes were then added to the cells and left to incubate for 4 h. Subsequently, the medium was discarded and the cells washed twice with pre-warmed OPTImem. Finally, 500 μl of OPTImem was added to the wells after which the cells were further incubated for 2-3 h. The cells were then analysed by fluorescence microscopy and confocal microscopy.

For confocal microscopy further preparation was necessary, as follows: Instead of adding final 400 μl OPTImem after the final washing steps the cells were fixed in PBS with 2.5% formaldehyde for 15 min room temperature. The cells were then washed 3× with PBS incubated with DRAQ5 (Biostatus Limited, UK) at 10 μM final concentration for 5 min at 37° C. after wish the cells were again washed twice with PBS and mounted in glass slides with DAKO fluorescent mounting medium. Confocal pictures were taken using a Zeiss LSM 510 microscope.

Oligonucletide Transfections

HeLa/Luc705 cells were pre-seeded at a density of 35,000 cells per well in a 24-well plate the day before transfection in order to have between 40% and 50% confluency the next day. Antisense oligonucleotide constructs were transfected by using Oligofectamine reagent (Invitrogen) and following the manufacturer's protocol. Cells were harvested in Luciferase lysis buffer (25 mM TAE, 10% glycerol, 1 mM EDTA, 1% Triton-X100) after 24 h and the level of luciferase expression was analysed based on a luciferase activity assay (Luciferase assay Kit, Biothema AB, Handen, Sweden). Total protein was measured using a BCA protein assay (Micro BCA™ protein assay kit, Thermo Scientific-Pierce Protein Research Products, Rockford, USA)

RT-PCR was done by isolating total RNA from cells with RNeasy plus kit (QIAGEN) from which a total of 3 ng of RNA was then used in each reaction (total volume per reaction was 20 μl) with the ONE STEP RT-PCR kit (QIAGEN) and following the manufacturers protocol. The primers used were:

```
Fwd-TTGATATGTGGATTTCGAGTCGTC;

Rev-TGTCAATCAGAGTGCTTTTGGCG.
```

The program for the RT-PCR was as follows: (55° C., 35 min+95° C., 15 min)×1 cycle+(94° C., 30 s+55° C., 30 s+72° C., 30 s)×29-30 cycles+72° C., 10 min final extension. The PCR products were analysed in a 2% agarose gel in 1×TBE buffer and visualized by SYBR-Gold (Invitrogen, Molecular Probes) staining. Gel images were captured by a Fluor-S gel documentation system (BioRad) with the Quantity One software (BioRad).

Results

1. $m_3G$-capped RNA Oligonucleotides are Able to Direct Nuclear Accumulation of a Cargo Protein in *Xenopus* oocytes The use of *Xenopus* oocytes for the study of nuclear transport systems is a very well characterized system offering many advantages for this type of studies [39-42]. Firstly, oocytes are very big cells with a large nucleus and easy to inject, secondly it is quite straightforward to study the isolated compartments (cytoplasm and nuclei) since the nuclei are relatively easy to isolate by manual dissection. A further very important feature is that the oocyte is a non-dividing cell which thereby maintains the integrity of its nuclear membrane throughout the experiments. Yet another reason to use the *Xenopus* oocyte for the initial study of the effect of $m_3G$-capped oligonucleotides was that many studies dealing with the import mechanism of U snRNAs were initially done using these cells [12, 18, 39, 43].

Figure 5:
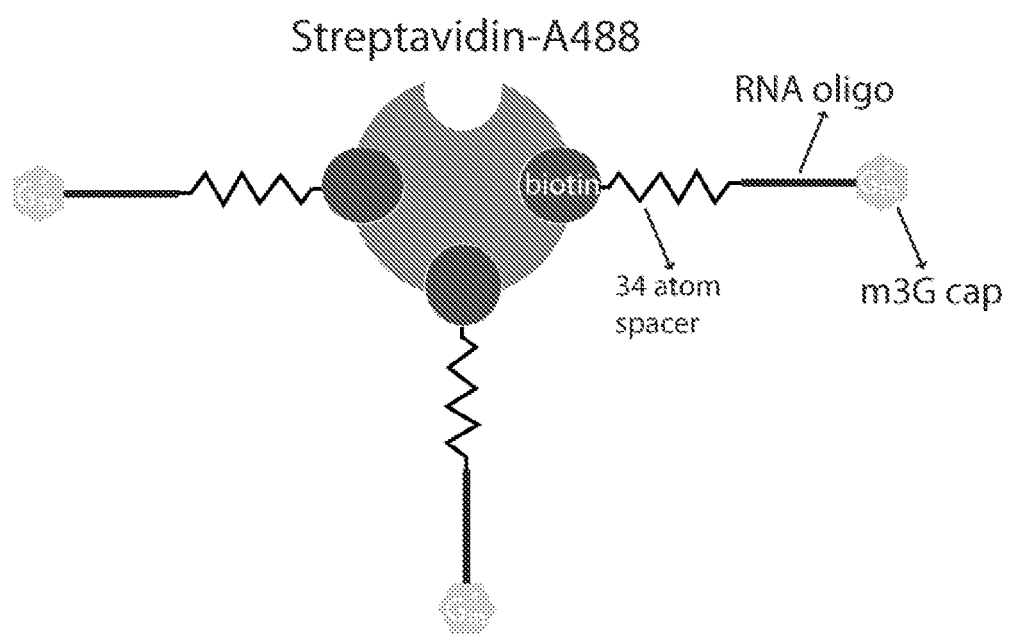
FIG. 5 is a schematic representation of Streptavidin-Alexa488 (STV)+, i.e. the m$_3$G-cap oligonucleotide construct used in the nuclear transport assays. Image proportions are exaggerated for a better understanding.

The inventors then decided to study the nuclear accumulation of a construct constituted of a fluorescent Streptavidin (STV) bound to 2-3 biotinylated 2'-O-methyl RNA oligonucleotides with (CAP-PM02) or without (p-PM02) $m_3G$-CAP modification (FIG. 5). The STV protein itself has a molecular weight of around 53 kDa and the addition of 2-4 biotinylated oligonucleotides equals a total MW for the construct of between 60-70 kDa. This should make it difficult for the STV-oligonucleotide construct to enter the nucleus by passive diffusion alone, since 45-50 kDa is the known cut-off of the nuclear pore. By having the cargo STV linked through a long spacer to the carrier oligo, the inventors were already gaining insight into the possible properties of the $m_3G$-CAP-oligo as a defined adaptor for enhancing nuclear transport a cargo when the NLS signal is not in its close proximity.

Injections into the oocyte cytoplasm of STV-oligonucleotide constructs with or without added $m_3G$-CAP were performed and after an incubation period of 4 h the nuclei were manually dissected to check for the relative amounts of STV protein that had been directed to the nuclear compartment. By analysing the amounts of STV recovered from the nuclear compartment with the use of Western Blot (FIGS. 6A and B), the inventors verified that the addition of $m_3G$-CAP oligonucleotides enhanced nuclear uptake at least 6-fold compared to the non-capped ones.

Figure 6A:
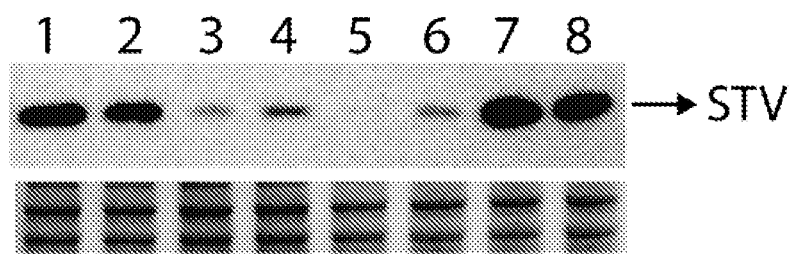
FIG. 6a is a western blot showing the accumulation of Streptavidin complexes in *Xenopus* oocyte nuclei after cytoplasmic injections.
Figure 6B:
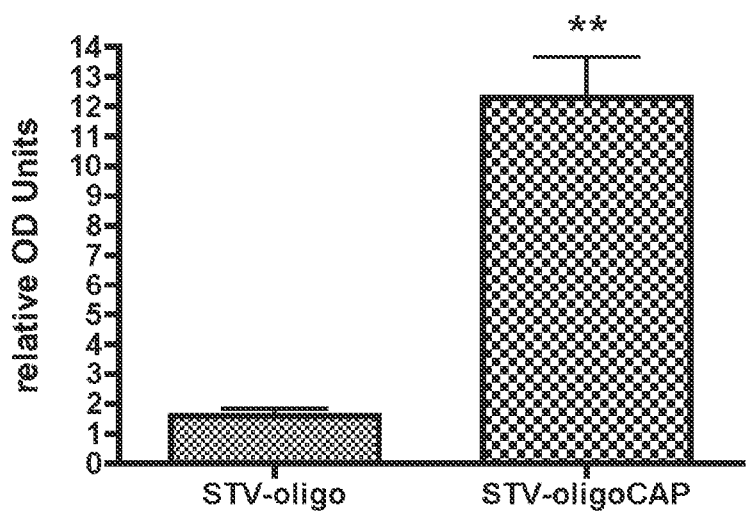
FIG. 6b is a graph showing the quantification of the western blot results by densitometry.

Oocytes were injected in the cytoplasm with either STV-RNA or STV-capRNA complexes and after 4 h incubation the nuclei were dissected and collected for Western Blot analysis. FIG. 6A shows western blot using anti-Streptavidin probing. Each lane corresponds to one group of 4 nuclei pooled together. Lanes 1-2-7-8: nuclei dissected from oocytes injected with STV-CAP-RNA; lanes 3-4-5-6: nuclei dissected from oocytes injected with STV-RNA. Lower panel shows a protein loading control by staining the gel with coomassie blue after transfer. FIG. 6B shows the result of quantification of Western Blot results by densitometry with normalization to the loading controls using Fluor-S MultiImager and Quantity One® software (BioRad) (SDs for n=4 are shown). **$P<0.005$.

There was still some STV recovered from the nucleus of oocytes injected with the non-capped oligonucleotide versions. This may be due to the fact that the outer nuclear membrane is in direct contact with the cytoplasm, hence there might be some residual unspecific binding of STV to the nuclear membrane. Due to this, the 6-fold higher nuclear uptake seen with the $m_3G$-cap may thus be regarded as the minimal difference. It can however not be excluded that some non-capped oligonucleotide diffuses passively into the nucleus since the total MW of the constructs is close to the nuclear pore cut-off size.

In addition to Western Blot analysis, the inventors performed fluorescent microscopy of isolated nuclei after cytoplasmic injections of the STV complexes. The nuclei were isolated in pairs each representing a cytoplasmic injection of STV with (nucleus 1) or without (nucleus 2) capped oligonucleotide. By putting the nuclei side by side it was easily seen that only the oocyte injected with STV-CAP oligonucleotide showed a green fluorescent nucleus while the nucleus from the other oocyte did not show any detectable fluorescence confirming the previous results of the western blot where the capped oligonucleotide conferred enhanced nuclear transport capacity to the STV-oligo complex.

2. $m_3G$-capped RNA Oligonucleotides are Able to Direct Nuclear Accumulation of a Cargo Protein in Mammalian Cells After Cytosolic Delivery by a Transfection Reagent The inventors also tested if the previous constructs would behave similarly when delivered to a mammalian cell line and, importantly, by a transfection method that resembles the delivery routes of many gene delivery protocols. For this, the inventors employed a method of protein and peptide delivery through the use of a reagent that promotes uptake of proteins into the cytosol of cells (PULSin) after endocytosis of protein-reagent complexes.

The feasibility of the method was first tested by using STV constructs bound to 2-3 biotinylated SV40-NLS peptides (pkkkrkv) or biotinylated SV40-mutatedNLS peptides (pktkrkv). When transfected to the cytosol of U2OS cells these constructs localized either in the nucleus (SV40-NLS construct >90%) or in the cytoplasm (SV40-mutNLS >90%) as observed by the detection of green fluorescence coming from the cargo STV-Alexa488 (data not shown).

After confirming the usability of the method for the planned nuclear transport studies, the inventors then tested the same constructs used in the *Xenopus* oocyte microinjections in the mammalian U2OS cell line (FIG. 7). Streptavidin-RNA complexes were transfected into U2OS cell lines by the use of PULSin reagent (protein transfection reagent). After 4 h incubation at 37° C., cells were washed and incubated for 2 h at 37° C. before fluorescent microscopy (B, D) and phase contrast pictures (A, C) were taken.

Some nuclei and cytoplasm of cells are marked by N and C, respectively, in the phase contrast pictures. Solid white arrows indicate examples of cells counted as positive for nuclear enrichment; Solid white arrowheads point to cells counted as negative for nuclear enrichment; open white arrowheads point to aggregates of fluorescent STV complexes that can occur during the transfection procedure; open rectangular boxes were drawn around the "STV-CAP nuclear bodies" formed by increased accumulation of STV complexes in the nucleus.

After transfection of the constructs, a completely different pattern between STV-PM02-CAP and STV-PM02-p was observed, both using 2-3× or 3-4× oligonucleotide to STV. The cells did not only show a higher nuclear fluorescence but also had a very specific pattern, where one could see very prominent nuclear bodies containing most of the STV fluorescence when it was attached to the $m_3G$-cap oligonucleotides. The size of these "STV-oligo bodies" were easily correlated to the amount of STV found in the nuclear compartment and corresponded to most of the nuclear fluorescence in contrast to an overall diffuse nuclear fluorescence that is seen when using STV-NLS peptides.

By using fluorescence microscopy, cells were also enumerated using specific criteria. Cells counted as positive for enhanced nuclear transport were characterized as having a more overall nuclear fluorescence with distinct bodies. Cells assigned as negative were characterized as having diffuse, preferential staining in the cytoplasm or both in the cytoplasm and nucleus (which argues for that the STV was not being actively targeted to the nuclei, but instead could diffuse in and out of the nuclear compartment). Following these criteria, the inventors found a very significant difference ($p<0.0001$) between the STV constructs bound by 3-4 $m_3G$-CAP-oligos (80% predominantly nuclear) and STV bound by 3-4 non-CAP-oligos (92% predominant cytoplasmic or overall diffuse staining). For the STV constructs carrying 2-3 oligos the percentages were 92% nuclear and 81% cytoplasmic respectively for $m_3G$-CAP and nonCAP attached oligos. It should be noted that when these STV-oligo constructs were created, together with the PULSin reagent, some aggregates were still remaining in the wells (these were visible as random bright spots of fluorescence of irregular shapes).

Confocal microscopy was used in order to further confirm the nuclear location of the STV-oligo-CAP (Not shown). The line trace profile graphs clearly show the co-localization of the nuclear stain (DRAQ5 stain represented by blue colour; blue line) with the fluorescent STV-oligo-CAP constructs (ALEXA488 green fluorescence; green line). Inversely, when using the STV-oligo constructs with no m$_3$G-CAP the line trace profile clearly shows an exclusive cytoplasmic localization. It is possible to see in the confocal images as well as in the regular epifluorescence images (FIG. 7) that some fluorescent STV-CAP complexes are outside the nucleus. Without wishing to be bound by any theory, the inventors believe that these are complexes still entrapped in vesicles in the cytoplasm or some form of irregular aggregates of the same complexes. This happened both for the non-CAP and CAP-STV transfected complexes.

In a further experiment, biotinylated locked nucleic acid (LNA) oligos were hybridized to m$_3$G-capped or non-capped oligonucleotides and then bound to Streptavidin. The same procedure as above was used to obtain the fluorescent microscopy pictures.

The results are shown in FIG. 7b. In panel A, LNA oligos were hybridized to non-capped oligos and in panel B, LNA oligos were hybridized to m$_3$G-capped oligos. The letters "n" and "c" show the localization of the nucleus and cytoplasm respectively. Strong nuclear accumulation was seen only when using the LNA oligos hybridized to m$_3$G-capped oligos.

The results of FIG. 7a are also presented in numeric form, in Table 2 below:

TABLE 2

Localization of fluorescent Streptavidin bound to 3-4 biotinylated 2'-O-methyl RNA oligonucleotides with or without m$_3$G-CAP-oligos

| STV-oligo2 | Predominant nuclear enrichment/distinct nuclear body formation | Predominant cytoplasmic or diffuse fluorescence both in cytoplasm and nucleus |
|---|---|---|
| With m$_3$G-CAP | 164 (80%) | 40 (20%) |
| Without m$_3$G-CAP | 11 (8%) | 130 (92%) |

*** p value < 0.0001

3. m$_3$G-capped 2'-O-methyl RNA Antisense Oligonucleotides have Increased Efficiency in a Splice Correction Assay Intron splicing is a mechanism occurring only in the nuclei of cells and for this reason the inventors used a splice correction assay to check for any increased activity of splice antisense oligos that could arise from their possible nuclear enrichment by the use of the m3G-CAP signal. The inventors used HeLa/Luc705 cells stably expressing a luciferase gene, where the coding region was interrupted by a mutated beta-globin intron at position 705. By targeting the region containing the mutation with antisense oligos one can redirect the splicing so that the luciferase mRNA is successfully translated into protein [43].

The oligonucleotide used for this study was a 2'-O-methyl oligoribonucleotide based on the same sequence as reported by Kang et al [43] but with a 3nt addition (AUA) to its 5' end. The oligonucleotide included an overhanging phosphate group at this same 5' end that was used later for the addition of the m$_3$G-CAP (m$_3$GpppAUA-).

After transfection of both oligonucleotide versions, with (oligo1CAP) or without (oligo1) m3G-CAP addition, it was found that the increase of luciferase activity relatively to untreated HeLa/Luc705 was dose dependent and that the capped antisense oligonucleotide had an increasingly higher activity across the concentration range tested. At the highest concentration tested there was an approximately 7.9-fold luciferase activity increase for the m$_3$G-capped oligonucleotide version and only 2.3-fold for the uncapped version (FIG. 8a). Thus, a maximum of 3.4-fold increase in efficiency was observed when using the m$_3$G-CAP signal.

A control oligonucleotide with a scrambled sequence was also tested at the highest concentration with or without m$_3$G-CAP. Both versions had no effect in correcting aberrant luciferase splicing attesting to that the m$_3$G-CAP addition had no effect itself in restoring luciferase activity.

The inventors confirmed the luciferase activity results with RT-PCR to directly show that the increase in luciferase activity was due to a correction of the aberrantly spliced luciferase by the antisense oligonucleotides. By subjecting total RNA from the treated cells to RT-PCR, it was shown that restoration of luciferase activity is correlated with an increase in the correctly spliced pre-mRNA and this was always more efficient when having capped-oligonucleotides compared to non-capped (See FIG. 8b, where the upper ban (268 bp) and lower band (142 bp) correspond to the aberrant and correct luciferase mRNA, respectively. Cp1 and p1 correspond to the antisense oligonucleotide (AS705) with (oligo Cp1) or without (oligo p1) m$_3$G-CAP added. Cp2 and p2 correspond to the scrambled (control) antisense oligonucleotide with (oligo Cp2) or without (oligo p2) m$_3$G-CAP).

In correlation to the previous results achieved with the cargo transport, this effect is most likely also due to a preferential accumulation of the antisense oligonucleotide in the nucleus. Despite the fact that the oligonucleotide itself is small enough to transverse through the nuclear pores by diffusion, by having an additional signal for nuclear targeting it is conceivable that this will shift the equilibrium in the direction of the nuclear compartment.

Example 2

Synthesis of m$_3$G-cap Structure for Stability Studies, m$_3$GpppAOMe (16)

Synthesis of 3'-O-Benzoyl-N$^6$-butyryl-2'-O-methyladenosine 9

N-Butyryl-5'-O-monomethoxytrityl-2'-O-methyladenosine 7 (100 mg, 0.16 mmol) was dried by evaporation of added dry pyridine (5 mL) under reduced pressure and finally by keeping on a vacuum pump for 30 min. Dry pyridine was added (2 mL) and the solution was put into ice-bath whereupon benzoyl chloride was added (1.2 eq, 0.19 mmol, 22.2 µL) and after 10 min the ice-bath was removed and the reaction was allowed to warm up and was then left stirring overnight at room temperature. A small amount of NaHCO$_3$ (aq. sat.) was added and the solvent was evaporated under reduced pressure. Dichloromethane was added and the organic phase was washed with NaHCO$_3$ (aq. sat. 2×). The organic phase was collected, dried (MgSO$_4$), filtered and concentrated. Evaporation of added toluene (2×) and dichloromethane (2×) was done to remove traces of pyridine. The remaining crude material of compound 8 was dissolved in 80% acetic acid (10 mL) and allowed to react at room temperature for 4 h. after which deprotection of 5'-monomethoxytrityl was complete (TLC, mass). The solution was concentrated and added toluene (2×) and dichloromethane (2×) evaporated under reduced pressure to remove excess acetic acid. The compound was purified on silica gel column chromatography using a gradient of methanol in dichloromethane (0-5%). Yield 80% of compound 9. $^1$H NMR (CDCl$_3$) δ 1.04 (3H, t, J=7.4 Hz), 1.80 (2H, m), 2.92 (2H, t, J=7.4 Hz), 3.31 (3H, s), 3.96 (2H, m), 4.51 (1H, s), 4.87 (1H, m), 5.90 (1H, d, J=4.9 Hz), 6.01 (1H, d, J=7.9 Hz), 6.32 (1H, d, J=9.9 Hz), 7.27 (2H, m), 7.51 (1H, m), 8.12 (2H, m), 8.18 (1H, s), 8.70 (1H, s), 9.27 (1H, s), $^{13}$C NMR δ 13.9, 18.4, 40.0, 59.3, 63.1, 72.7, 77.4, 81.4, 86.8, 89.9, 123.7, 128.1, 128.9, 129.8, 133.7, 143.5, 150.2, 152.1, 165.8, 173.5, MS (ES-TOF) m/z calculated: 455.18. found: 455.38.

Synthesis of 3'-O-Benzoyl-N$^6$-butyryl-2'-O-methyladenosine 5'-phosphate 10

3'-O-Benzoyl-N$^6$-butyryl-2'-O-methyladenosine 5 (57 mg, 0.125 mmol) was dried by evaporation of added dry pyridine (5 mL) and then further dried on a vacuum pump for 30 min. The compound was dissolved in a solution of H-pyrophosphonate (0.63 mL of the stock solution synthesized in situ from H$_3$PO$_3$, 1.62 g and 1.35 mL PVCl in dry pyridine, 10 mL). The reaction was left stirring overnight at room temperature.

The solution was concentrated and traces of pyridine was removed by evaporation of added toluene (2×) and dichloromethane (2×). The compound was purified by silica gel column chromatography using a gradient of methanol in dichloromethane (0-15%). Yield 71% of compound 10 (55 mg). $^1$H NMR (CDCl$_3$) δ 1.02 (3H, t, J=7.4 Hz), 1.17 (3H, s), 1.28 (9H, t, J=7.2 Hz), 1.79 (2H, m), 2.86 (2H, t, J=7.4 Hz), 3.05 (6H, t, J=7.2 Hz), 3.36 (3H, s), 4.20 (2H, m), 4.52 (1H, s), 4.70 (1H, m), 5.77 (1H, dd, J=2.0 Hz, J=4.9 Hz), 6.17 (½H, s), 6.38 (1H, d, J=6.8 Hz), 7.46 (2H, m), 7.59 (1H, m), 7.73 (½H, s), 8.09 (2H, m), 8.69 (1H, s), 8.80 (1H, s), 8.95 (1H, s), $^{13}$C NMR δ 8.8, 15.0, 18.5, 27.6, 38.6, 39.8, 45.6, 53.6, 59.2, 63.3, 72.4, 77.5, 83.0, 83.4, 86.1, 89.9, 122.1, 128.7, 129.4, 130.0, 133.7, 140.0, 149.2, 151.9, 152.7, 165.8, 173.2, 182.5, $^{31}$P NMR δ 5.4, dt, J=619 Hz, J=5.9 Hz MS (ES-TOF) m/z calculated: 518.14. found: 518.07.

Synthesis of 2'-O-methyladenosine 5'-phosphate 11

3'-O-Benzoyl-N$^6$-butyryl-2'-O-methyl adenosine 5'-H-phosphonate 10 (55 mg, 0.088 mmol) was dried by evaporation of added dry pyridine (5 mL) and 30 min drying on a vacuum pump. To the compound was added pyridine (0.8 mL), triethylamine (5 eq, 0.44 mmol, 61 µL) and trimethyl silyl chloride (5 eq, 0.44 mmol, 55.7 µL). The reaction was stirred for 15 min at room temperature, whereupon a solution of I$_2$/H$_2$O in pyridine (1.1 eq 12, 24 mg, 50 µL H$_2$O, 500 µL pyridine) was added. After an additional 5 min a sample was taken and analysed by $^{31}$P NMR which showed complete oxidation. A drop of ethanethiol was added to achieve a colorless solution, the solvent was removed under reduced pressure and the crude compound was dissolved in MeOH/NH$_3$ (sat.). The mixture was left overnight at room temperature, whereupon the solvent was removed under reduced pressure and the solid was dissolved in water. The aqueous solution was washed with diethyl ether (2×). The water layer was then collected, concentrated under reduced pressure and purified by RP-HPLC using a triethyl ammonium acetate buffer pH 6.5. RT=14 min (0-20 min 12% B, B=50% CH$_3$CN). Yield 37% of compound 11 as triethyl ammonium salt (18.4 mg). $^{31}$P NMR (D$_2$O) δ-1.02, $^{13}$C NMR δ 7.3, 22.4, 45.7, 57.2, 63.0, 68.3, 70.7, 82.3, 84.1, 84.4, 118.2, 126.5, 140.2, 148.2, 151.8, 154.6, 180.4, 199.5, MS (ES-TOF) m/z calculated: 361.08. found: 361.10.

m$_3$GpppAOMe (16).

The HPLC purified triethyl ammonium salt of the 3mGpp imidazolide (5) (0.7 mg, 0.00095 mmol) was dissolved in N-ethylmorpholine buffer (20 mM, 0.1 mL) containing MnCl$_2$ (0.017 mmol, 2.7 mg) and vortexed. This mixture was added to the solid compound 11 (9.6 mg, 0.017 mmol). The reaction was vortexed in an eppendorf tube at room temperature overnight. The product was purified by RP-HPLC using a triethyl ammonium acetate buffer pH 6.5. RT=14.8 min (0-20 min 20% B, B=50% CH$_3$CN). Yield 58%, 14 ODU, 0.63 mg of compound 11 as triethyl ammonium salt. MS (ES-TOF) m/z calculated: 827.15. found: 827.32. The synthesis scheme for compounds 16 and 17 is shown in FIG. 9.

Example 3

Synthesis of Methylenephosphonate Modified m$_3$G-cap Structure for Stability Studies, m$_3$GpCH$_2$pppAOMe (17)

Synthesis of N$^2$,N$^2$,-dimethylguanosine 13

2',3',5'-tri-O-acetyl-N$^2$,N$^2$,-dimethylguanosine 1 (2.15 g, 4.9 mmol) was dissolved in saturated MeOH/NH$_3$ and left overnight. The solvent was evaporated under reduced pressure and the crude compound was dissolved in water. The water solution was washed twice with dichloromethane, concentrated, freeze-dried and then used as such in the next step. MS (ES-TOF) m/z calculated: 311.12. found: 311.32.

Synthesis of N$^2$,N$^2$,-dimethylguanosine 5'-methylenepyrophosphate 14

Nucleoside 13 (311 mg, 1 mmol) was suspended in PO(OMe)$_3$ (3 mL) and put on an ice-bath. Methylenebis(phosphonic dichloride) (2 eq, 2 mmol, 494 mg) dissolved in PO(OMe)$_3$ (3 mL) was added to the stirred cooled nucleoside solution under argon atmosphere. After 10 min when the solution became clear, mass spectra indicated full conversion to 5'-methylenepyrophosphate. Small aliquots of triethyl ammonium acetate buffer (from HPLC) pH 6.5 was added and the reaction was allowed to stand for 15 min. The whole reaction mixture was transferred to a separation funnel and the water layer was washed with dichloromethane (2×). The water phase was collected and freeze-dried. MS (ES-TOF) m/z calculated: 468.07. found: 468.22.

Synthesis of N$^7$,N$^2$,N$^2$-trimethylguanosine 5'-methylenepyrophosphate 15

Compound 14, crude after freeze-drying, (0.5 mmol) was suspended in dry DMF (6 mL) and methyl iodide (0.618 mL, 10 mmol, 20 eq) was added. The reaction was stirred at 40° C. for 5 h. The solvent was evaporated and the product was dissolved in water and purified by preparative RP-HPLC using a gradient of buffer B in buffer A (0-10% B over 30 min). Evaporation of collected fractions gave compound 15 as the tris(triethylamine)salt. RT=20.1 min. Yield 20 mg, 5.2% after 3 steps. $^{31}$P-NMR (D2O): δ=5.9 and 9.6 ppm. MS (ES-TOF) m/z calculated: 482.08. found: 484.29.

Synthesis of 2'-O-methyl adenosine 5'-phosphorylimidazolide 12

Compound 11 (9 mg, 0.016 mmol) was dissolved in DMF (0.4 mL) containing triethylamine (0.02 mL) and tri-n-butylamine (0.02 mL). The mixture was stirred at room temperature and imidazole (5.4 mg, 0.08 mmol, 5 eq) was added, followed by triphenylphosphine (21 mg, 0.08 mmol, 5 eq) and di-2-pyridyldisulfide (17.5 mg, 0.08 mmol, 5 eq) and then left for 24 h. The solvent was evaporated under reduced pressure and the crude product was dissolved in water and purified by RP-HPLC using a gradient of buffer B in buffer A (0-15% of B over 30 min). Evaporation of collected fractions gave compound 12 as the tris(triethylammine)salt. RT=28.6 min. Yield 6.8 mg, 82%. MS (ES-TOF) m/z calculated: 410.11. found: 410.10.

m$_3$GpCH$_2$ppAOMe 17.

HPLC purified imidazolide (12), as triethylammonium salt, (6.8 mg, 0.013 mmol) was dissolved in aqueous N-ethyl morpholine buffer (20 mM, 0.1 mL) containing MnCl$_2$ (0.013 mmol, 2.14 mg). The mixture was vortexed and added to dry compound 15 (5 mg, 0.063 mmol). The reaction was vortexed in an eppendorf tube at room temperature for four days. The product was purified by RP-HPLC using a triethylammonium acetate buffer pH 6.5. RT=19.7 min (0-30 min 25% B, B=50% CH$_3$CN). Yield 1%, 0.93 ODU, of compound 17 as triethylammonium salt. MS (ES-TOF) m/z calculated: 826.14. found: 826.60.

Example 4

Stability Studies of Models of the Native Cap (16) and a Methylenephosphonate Cap (17) in Cell Medium Containing 10% Serum and Cytosolic Extract (1-3 mg/mL Total Protein)

Compounds 16 and 17 were dissolved in water to give a concentration where 72 µL of stock solution dissolved diluted to 1 mL in water gave a UV-absorbance of 0.07 at 260 nm. A 72 µL aliquot of the stock solution of 16 or 17, respectively, was added to 300 µL of cell medium (containing 10% human serum) or cellular extract (containing 1.3 mg/mL of total protein). Immediately after adding the cell medium or cellular extract the mixture was vortexed and the first aliquots (2×46 µL) were taken out to a 5K Millipore NMWL filters, diluted with 72 µL water, vortexed and centrifuged through the filter for 3 min at 13.4×10$^3$ rpm. Another 72 µL of water was added to each tube and the procedure (centrifugation) was repeated as above. The two filtrates were collected and analysed by RP-HPLC using a triethylammonium acetate buffer pH 6.5. RT=17.2 min (0-30 min 5-20% B, B=50% CH$_3$CN). Separated samples were collected and analyzed by MS (ES-TOF). The HPLC chromatograms were integrated and the amount of dimer in the initial sample was normalized to be 100%. After taking this "zero" time point (after 5 min at room temperature) reaction mixtures were allowed to react at 37° C. The 3 time points were taken and same sample preparation procedure, HPLC-analysis and integration was repeated for each. The integrated areas as percentage of the normalized "zero" time point area were plotted against incubation time using the KaleidaGraph program.

FIGS. 11 and 12 show the time dependence of the disappearance of the native m$_3$G-cap (16) and the methylenephosphonate modified m$_3$G-cap (17) in cell medium with 10% human serum (duplicate runs), which displays increased stability towards degradation in biological liquids, for the compound with the modified triphosphate function.

FIG. 13 shows a comparison of the time dependence of the disappearance of compounds 16 (squares) and 17 (circles) in cytosolic extract (1.3 mg/mL of total protein) which shows increased stability towards degradation in a cytoplasmic environment, for the compound with the modified triphosphate function.

Although the invention has been described with regard to its preferred embodiments, which constitute the best mode presently known to the inventor, it should be understood that various changes and modifications as would be obvious to one having the ordinary skill in this art may be made without departing from the scope of the invention as set forth in the claims appended hereto.

REFERENCES

1. Görlich, D. and Mattaj, I. W. (1996) Nucleocytoplasmic transport. Science, 271, 1513-1518.
2. Lange, A., Mills, R. E., Lange, C. J., Stewart, M., Devine, S. E. and Corbett, A. H. (2006) Classical nuclear localization signals: definition, function, and interaction with importin alpha. J Biol Chem, 282, 5101-5105.
3. Jäkel, S. and Görlich, D. (1998) Importin beta, transportin, RanBP5 and RanBP7 mediate nuclear import of ribosomal proteins in mammalian cells. EMBO J., 17, 4491-4502.
4. Görlich, D., Pante, N., Kutay, U., Aebi, U. and Bischoff, F. R. (1996) Identification of different roles for RanGDP and RanGTP in nuclear protein import. EMBO J, 15, 5584-5594.
5. Izaurralde, E., Kutay, U., von Kobbe, C., Mattaj, I. W. and Görlich, D. (1997) The asymmetric distribution of the constituents of the Ran system is essential for transport into and out of the nucleus. EMBO J, 16, 6535-6547.
6. Kitao, S., Segref, A., Kast, J., Wilm, M., Mattaj, I. W. and Ohno, M. (2008) A compartmentalized phosphorylation/dephosphorylation system that regulates U snRNA export from the nucleus. Mol Cell Biol, 28, 487-497.
7. Golembe, T. J., Yong, J. and Dreyfuss, G. (2005) Specific sequence features, recognized by the SMN complex, identify snRNAs and determine their fate as snRNPs. Mol Cell Biol, 25, 10989-11004.
8. Yong, J., Golembe, T. J., Battle, D. J., Pellizzoni, L. and Dreyfuss, G. (2004) snRNAs contain specific SMN-binding domains that are essential for snRNP assembly. Mol Cell Biol, 24, 2747-2756.
9. Friesen, W. J. and Dreyfuss, G. (2000) Specific sequences of the Sm and Sm-like (Lsm) proteins mediate their interaction with the spinal muscular atrophy disease gene product (SMN). J Biol Chem, 275, 26370-26375.
10. Fischer, U., Liu, Q. and Dreyfuss, G. (1997) The SMN-SIP1 complex has an essential role in spliceosomal snRNP biogenesis. Cell, 90, 1023-1029.

11. Mouaikel, J., Narayanan, U., Verheggen, C., Matera, A. G., Bertrand, E., Tazi, J. and Bordonne, R. (2003) Interaction between the small-nuclear-RNA cap hypermethylase and the spinal muscular atrophy protein, survival of motor neuron. EMBO Rep, 4, 616-622.
12. Plessel, G., Fischer, U. and Lührmann, R. (1994) m₃g-cap hypermethylation of U1 small nuclear ribonucleoprotein (snRNP) in vitro: evidence that the U1 small nuclear RNA-(guanosine-N2)-methyltransferase is a non-snRNP cytoplasmic protein that requires a binding site on the Sm core domain. Mol Cell Biol, 14, 4160-4172.
13. Narayanan, U., Ospina, J. K., Frey, M. R., Hebert, M. D. and Matera, A. G. (2002) SMN, the spinal muscular atrophy protein, forms a pre-import snRNP complex with snurportin1 and importin beta. Hum. Mol. Genet., 11, 1785-1795.
14. Huber, J., Cronshagen, U., Kadokura, M., Marshallsay, C., Wada, T., Sekine, M. and Lührmann, R. (1998) Snurportin1, an m3G-cap-specific nuclear import receptor with a novel domain structure. EMBO J., 17, 4114-4126.
15. Mitrousis, G., Olia, A. S., Walker-Kopp, N. and Cingolani, G. (2008) Molecular basis for the recognition of snurportin 1 by importin beta. J Biol Chem, 283, 7877-7884.
16. Wohlwend, D., Strasser, A., Dickmanns, A. and Ficner, R. (2007) Structural basis for RanGTP independent entry of spliceosomal U snRNPs into the nucleus. J Mol Biol, 374, 1129-1138.
17. Girard, C., Mouaikel, J., Neel, H., Bertrand, E. and Bordonné, R. (2004) Nuclear localization properties of a conserved protuberance in the Sm core complex. Exp. Cell Res., 299, 199-208.
18. Fischer, U. and Lührmann, R. (1990) An essential signaling role for the m₃g-cap in the transport of U1 snRNP to the nucleus. Science, 249, 786-790.
19. Strasser, A., Dickmanns, A., Schmidt, U., Penka, E., Urlaub, H., Sekine, M., Lührmann, R. and Ficner, R. (2004) Purification, crystallization and preliminary crystallographic data of the m3g-cap-binding domain of human snRNP import factor snurportin 1. Acta Crystallogr. D Biol. Crystallogr., 60, 1628-1631.
20. Strasser, A., Dickmanns, A., Lührmann, R. and Ficner, R. (2005) Structural basis for m3G-cap-mediated nuclear import of spliceosomal UsnRNPs by snurportin1. EMBO J., 24, 2235-2243.
21. Huber, J., Dickmanns, A. and Lührmann, R. (2002) The importin-beta binding domain of snurportin1 is responsible for the Ran- and energy-independent nuclear import of spliceosomal U snRNPs in vitro. J. Cell Biol., 156, 467-479.
22. Chen, P., Wang, J., Hope, K., Jin, L., Dick, J., Cameron, R., Brandwein, J., Minden, M. and Reilly, R. M. (2006) Nuclear localizing sequences promote nuclear translocation and enhance the radiotoxicity of the anti-CD33 monoclonal antibody HuM195 labeled with 111In in human myeloid leukemia cells. J Nucl Med, 47, 827-836.
23. Dean, D. A., Dean, B. S., Muller, S. and Smith, L. C. (1999) Sequence requirements for plasmid nuclear import. Exp Cell Res, 253, 713-722.
24. Wagstaff, K. M. and Jans, D. A. (2007) Nucleocytoplasmic transport of DNA: enhancing non-viral gene transfer. Biochem J, 406, 185-202.
25. Collas, P., Husebye, H. and Alestrom, P. (1996) The nuclear localization sequence of the SV40 T antigen promotes transgene uptake and expression in zebrafish embryo nuclei. Transgenic Res, 5, 451-458.
26. Zanta, M. A., Belguise-Valladier, P. and Behr, J. P. (1999) Gene delivery: a single nuclear localization signal peptide is sufficient to carry DNA to the cell nucleus. Proc Natl Acad Sci USA, 96, 91-96.
27. Brandén, L. J., Mohamed, A. J. and Smith, C. I. E. (1999) A peptide nucleic acid-nuclear localization signal fusion that mediates nuclear transport of DNA. Nat Biotechnol, 17, 784-787.
28. Brandén, L. J., Christensson, B. and Smith, C. I. E. (2001) In vivo nuclear delivery of oligonucleotides via hybridizing bifunctional peptides. Gene Ther, 8, 84-87.
29. Neves, C., Byk, G., Scherman, D. and Wils, P. (1999) Coupling of a targeting peptide to plasmid DNA by covalent triple helix formation. FEBS Lett, 453, 41-45.
30. Ludtke, J. J., Zhang, G., Sebestyén, M. G. and Wolff, J. A. (1999) A nuclear localization signal can enhance both the nuclear transport and expression of 1 kb DNA. J. Cell. Sci., 112 (Pt 12), 2033-2041.
31. Subramanian, A., Ranganathan, P. and Diamond, S. L. (1999) Nuclear targeting peptide scaffolds for lipofection of nondividing mammalian cells. Nat Biotechnol, 17, 873-877.
32. Sawai, H., Wakai, H. and Nakamura-Ozaki, A. (1999) Synthesis and Reactions of Nucleoside 5'-Diphosphate Imidazolide. A Nonenzymatic Capping Agent for 5'-Monophosphorylated Oligoribonucleotides in Aqueous Solution. J Org Chem, 64, 5836-5840.
33. Sekine, M., Kadokura, M., Satoh, T., Seio, K., Wada, T., Fischer, U., Sumpter, V. and Lührmann, R. (1996) Chemical Synthesis of a 5'-Terminal TMG-Capped Triribonucleotide m(3)(2,2,7)G(5)(')pppAmpUmpA of U1 RNA. J Org Chem, 61, 4412-4422.
34. Li, P., Xu, Z., Liu, H., Wennefors, C. K., Dobrikov, M. I., Ludwig, J. and Shaw, B. R. (2005) Synthesis of alpha-P-modified nucleoside diphosphates with ethylenediamine. J Am Chem Soc, 127, 16782-16783.
35. Ludwig, J. and Eckstein, F. (1989) Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one. J Org Chem, 54, 631-635.
36. Li, P. and Shaw, B. R. (2004) Convenient synthesis of nucleoside borane diphosphate analogues: deoxy- and ribonucleoside 5'-P(alpha)-boranodiphosphates. J Org Chem, 69, 7051-7057.
37. Han, Q., Gaffney, B. L. and Jones, R. A. (2006) One-flask synthesis of dinucleoside tetra- and pentaphosphates. Org Lett, 8, 2075-2077.
38. Kang, S. H., Cho, M. J. and Kole, R. (1998) Up-regulation of luciferase gene expression with antisense oligonucleotides: implications and applications in functional assay development. Biochemistry, 37, 6235-6239.
39. Mattaj, I. W. (1986) Cap trimethylation of U snRNA is cytoplasmic and dependent on U snRNP protein binding. Cell, 46, 905-911.
40. Pante, N. (2006) Use of intact *Xenopus* oocytes in nucleocytoplasmic transport studies. Methods Mol Biol, 322, 301-314.
41. Bonner, W. M. (1975) Protein migration into nuclei. II. Frog oocyte nuclei accumulate a class of microinjected oocyte nuclear proteins and exclude a class of microinjected oocyte cytoplasmic proteins. J Cell Biol, 64, 431-437.
42. Dabauvalle, M. C. and Franke, W. W. (1982) Karyophilic proteins: polypeptides synthesized in vitro accumulate in the nucleus on microinjection into the cytoplasm of amphibian oocytes. Proc Natl Acad Sci USA, 79, 5302-5306.
43. Stefanovic, B., Hackl, W., Lührmann, R. and Schümperli, D. (1995) Assembly, nuclear import and function of U7 snRNPs studied by microinjection of synthetic U7 RNA into *Xenopus* oocytes. Nucleic Acids Res, 23, 3141-3151.
44. Rollenhagen, C., Muhlhausser, P., Kutay, U. and Pante, N. (2003) Importin beta-depending nuclear import pathways: role of the adapter proteins in the docking and releasing steps. Mol Biol Cell, 14, 2104-2115.
45. Rollenhagen, C. and Pante, N. (2006) Nuclear import of spliceosomal snRNPs. Can J Physiol Pharmacol, 84, 367-376.
46. Rongbin Ge, Mathias G. Svahn, Oscar E. Simonson, Abdalla J. Mohamed, Karin E. Lundin, C. I. Edvard Smith, Sequence-specific inhibition of RNA polymerase III-dependent transcription using Zorro locked nucleic acid (LNA), The Journal of Gene Medicine, 2007, Volume 10, Issue 1, Pages 101-109.

The invention claimed is:

1. A complex for facilitating transmembrane transport of a molecular cargo into the nucleus of a mammalian cell, wherein said complex comprises a molecular cargo coupled to a synthetic m₃G-CAP or an analogue thereof, wherein said molecular cargo is linked by covalent or non-covalent attachment to at least one modified 2,2,7-trimethylguanosine CAP structure as specified in Formula (I)

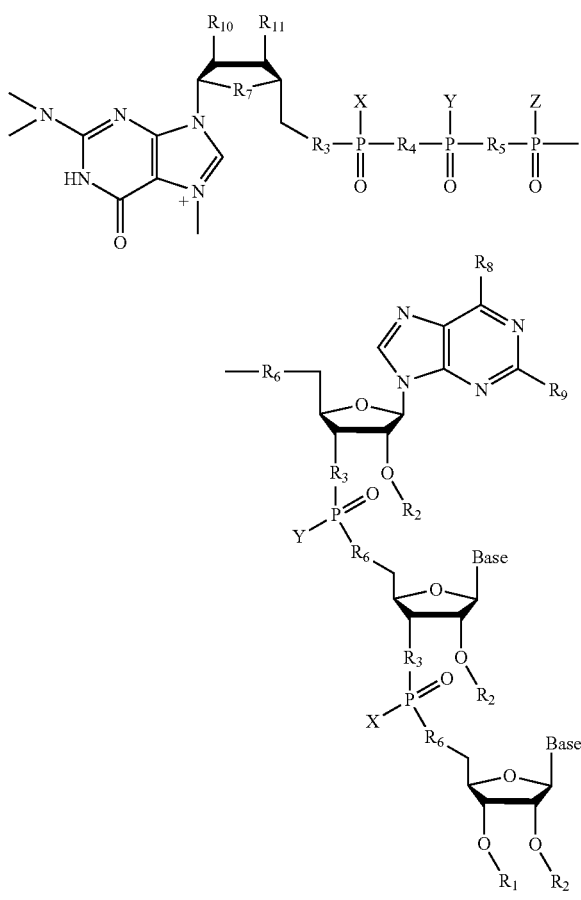

(I)

wherein $R_1$ is a cargo attached directly or a mono-, di- or oligo-nucleotide (modified or unmodified) followed by a cargo unless the cargo is attached through $R_2$ then $R_1$ is a hydroxyl or a phosphate mono or diester;

$R_2$ is methyl or any unsubstituted or substituted alkyl group or is a cargo attached directly or a mono-, di- or oligo-nucleotide (modified or unmodified) followed by a cargo;

$R_3$ is O or $CH_2$;

$R_4$ is O or $CH_2$;

$R_5$ is O or $CH_2$;

$R_6$ is O or $CH_2$;

X is OH or SH, or salts thereof;

Y is OH or SH, or salts thereof;

Z is OH or SH, or salts thereof;

$R_7$ is O, Or $CH_2$;

$R_8$ is $NH_2$, H, or OH;

$R_9$ is H, $NH_2$ or OH;

$R_{10}$ is OH, or F; and $R_{11}$ is OH, Or $OCH_3$, and wherein "base" is a purine or a pyrimidine base selected from uracil, cytosine, adenine, quinine or thymine or derivatives thereof.

2. The complex according to claim 1, wherein $R_4$ and $R_5$ are $CH_2$.

3. The complex according to claim 1, wherein $R_5$ is O when $R_4$ is $CH_2$.

4. The complex according to claim 1, wherein $R_4$ is O when $R_5$ is $CH_2$.

5. The complex according to claim 1, further including phosphorothioate modifications of the compound, as either isomer, at one or more of the positions X, Y and Z.

6. The complex according to claim 1, wherein said molecular cargo comprises a therapeutic molecule chosen among natural and synthetic peptides, proteins, oligonucleotides, morpholino oligomers or nucleic acids linked to the above structure by a covalent linkage or by non-covalent interaction.

7. A method for transmembrane transport of a molecular cargo into the nucleus of a mammalian cell, wherein nuclear delivery of said molecular cargo is achieved by covalent or non-covalent attachment to at least one modified 2,2,7-trimethylguanosine CAP structure as specified in claim 1.

8. A medicament comprising a modified 2,2,7-trimethylguanosine CAP structure according to claim 1 or an analogue thereof.

9. A complex for facilitating transmembrane transport of a molecular cargo into the nucleus of a mammalian cell, wherein said complex comprises a molecular cargo coupled to a synthetic m₃G-CAP or an analogue thereof, wherein said molecular cargo is linked by covalent or non-covalent attachment to at least one modified 2,2,7-trimethylguanosine CAP structure as specified in Formula (I)

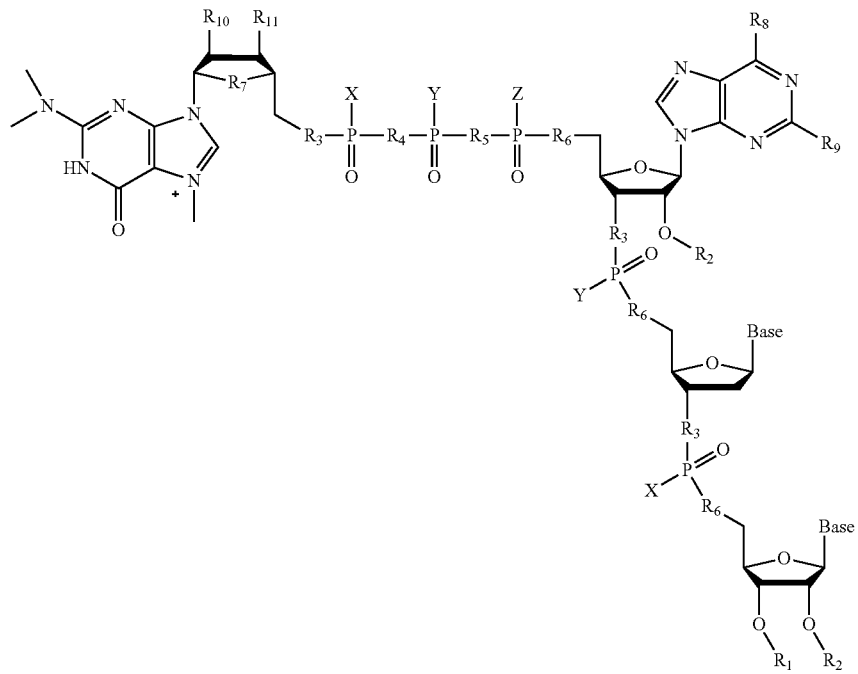

wherein
R₁ is a cargo attached directly or a mono-, di- or oligo-nucleotide (modified or unmodified) followed by a cargo unless the cargo is attached through R₂ then R₁ is a hydroxyl or a phosphate mono or diester;
R₂ is methyl or any unsubstituted or substituted alkyl group or is a cargo attached directly or a mono-, di- or oligo-nucleotide (modified or unmodified) followed by a cargo;
R₃ is O or CH₂;
R₆ is O or CH₂;
X is OH or SH, or salts thereof;
Y is OH or SH, or salts thereof;
Z is OH or SH, or salts thereof;
R₇ is O, Or CH₂;
R₈ is NH₂, H, or OH;
R₉ is H, NH₂ or OH;
R₁₀ is OH, or F; and
R₁₁ is OH, Or OCH₃,
wherein R₄ and R₅ are CH₂, or R₅ is O when R₄ is CH₂, or R₄ is O when R₅ is CH₂, and
wherein "base" is a purine or a pyrimidine base selected from uracil, cytosine, adenine, quinine or thymine or derivatives thereof.

* * * * *